US012655194B2

(12) United States Patent
Levin et al.

(10) Patent No.: US 12,655,194 B2
(45) Date of Patent: Jun. 16, 2026

(54) HLA CLASS II-RESTRICTED DRB T CELL RECEPTORS AGAINST RAS WITH G12V MUTATION

(71) Applicant: The United States of America, as represented by the Secretary, Department of Health and Human Services, Bethesda, MD (US)

(72) Inventors: Noam Levin, Rockville, MD (US); Frank J. Lowery, III, Clarksburg, MD (US); Maria R. Parkhurst, Ellicott City, MD (US); Steven A. Rosenberg, Potomac, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 750 days.

(21) Appl. No.: 18/015,781

(22) PCT Filed: Jul. 15, 2021

(86) PCT No.: PCT/US2021/041737
§ 371 (c)(1),
(2) Date: Jan. 12, 2023

(87) PCT Pub. No.: WO2022/015922
PCT Pub. Date: Jan. 20, 2022

(65) Prior Publication Data
US 2023/0257440 A1       Aug. 17, 2023

Related U.S. Application Data

(60) Provisional application No. 63/052,502, filed on Jul. 16, 2020.

(51) Int. Cl.
| | |
|---|---|
| C07K 14/725 | (2006.01) |
| A61K 40/11 | (2025.01) |
| A61K 40/19 | (2025.01) |
| A61K 40/24 | (2025.01) |
| A61K 40/32 | (2025.01) |
| A61K 40/42 | (2025.01) |
| A61P 35/00 | (2006.01) |
| C07K 14/705 | (2006.01) |
| C12N 15/63 | (2006.01) |
| G01N 33/575 | (2026.01) |

(52) U.S. Cl.
CPC .......... *C07K 14/7051* (2013.01); *A61K 40/11* (2025.01); *A61K 40/19* (2025.01); *A61K 40/24* (2025.01); *A61K 40/32* (2025.01); *A61K 40/42* (2025.01); *A61K 40/4201* (2025.01); *A61K 40/4253* (2025.01); *A61P 35/00* (2018.01); *C12N 15/63* (2013.01); *G01N 33/575* (2026.01); *A61K 2239/50* (2023.05)

(58) Field of Classification Search
None
See application file for complete search history.

(56) References Cited

U.S. PATENT DOCUMENTS

| | | | |
|---|---|---|---|
| 8,034,334 | B2 | 10/2011 | Dudley et al. |
| 8,383,099 | B2 | 2/2013 | Dudley et al. |
| 10,556,940 | B2 | 2/2020 | Tran et al. |
| 11,207,394 | B2 | 12/2021 | Wang et al. |
| 2012/0244133 | A1 | 9/2012 | Rosenberg et al. |
| 2019/0085046 | A1 | 3/2019 | Yoseph et al. |

FOREIGN PATENT DOCUMENTS

| | | | | |
|---|---|---|---|---|
| JP | 2017-536825 A | 12/2017 | | |
| JP | 2018-535647 A | 12/2018 | | |
| WO | WO-2012038055 A1 * | 3/2012 | .............. | A61P 43/00 |
| WO | WO-2019112941 A1 * | 6/2019 | ......... | C07K 16/2833 |
| WO | WO-2019157279 A1 * | 8/2019 | ........... | C12N 5/0636 |

OTHER PUBLICATIONS

Riley and Baker. The intersection of affinity and specificity in the development and optimization of T cell receptor based therapeutics. Seminars in Cell & Developmental Biology 84 (2018) 30-41. (Year: 2018).*
ACS. Cancer Risk and Prevention Webpage. Mar. 21, 2025. (Year: 2025).*
Cafri et al. "Memory T cells targeting oncogenic mutations detected in peripheral blood of epithelial cancer patients." *Nature Communications*, 10: 449, pp. 1-9 (2019).
Cohen et al., "Enhanced Antitumor Activity of Murine-Human Hybrid T-Cell Receptor (TCR) in Human Lymphocytes Is Associated With Improving Pairing and TCR/CD3 Stability", *Cancer Research*, 66(17): 8878-8886 (2006).
Cohen et al., "Enhanced antitumor activity of T cells engineered to express T-cell receptors with a second disulfide bond", *Cancer Research*, 67(8): 3898-3903 (2007).
Cox et al. "Drugging the undruggable RAS: Mission possible?" *Nature Reviews. Drug* Discovery 13(11): 828-851 (2014).
Dudley et al., "Generation of Tumor-Infiltrating Lymphocyte Cultures for Use in Adoptive Transfer Therapy for Melanoma Patients", *Journal of Immunotherapy*, 26(4):332-342 (2003).
Haga-Friedman et al., "Incorporation of transmembrane hydrophobic mutations in the TCR enhance its surface expression and T cell functional avidity", *Journal of Immunology*, 188(11): 5538-5546 (2012).

(Continued)

*Primary Examiner* — Julie Wu
*Assistant Examiner* — Amu M. Chattin
(74) *Attorney, Agent, or Firm* — Leydig, Voit & Mayer

(57) ABSTRACT
Disclosed is an isolated or purified T cell receptor (TCR), wherein the TCR has antigenic specificity for a mutated human RAS amino acid sequence with a substitution of glycine at position 12 with valine. The TCRs may recognize G12V RAS presented by an HLA-DR heterodimer. Related polypeptides and proteins, as well as related nucleic acids, recombinant expression vectors, host cells, populations of cells, and pharmaceutical compositions are also provided. Also disclosed are methods of detecting the presence of cancer in a mammal and methods of treating or preventing cancer in a mammal.

41 Claims, 3 Drawing Sheets

Figure 1A:
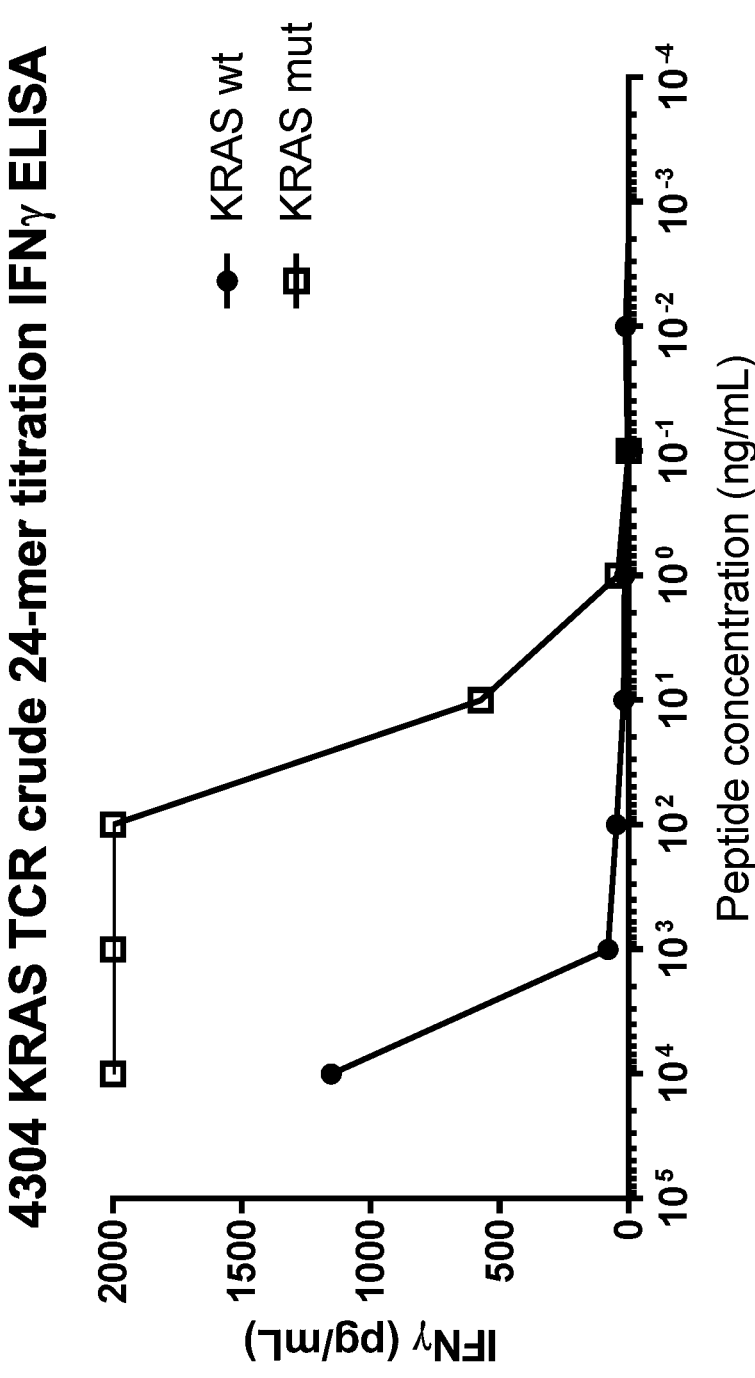

Specification includes a Sequence Listing.

(56) References Cited

OTHER PUBLICATIONS

International Searching Authority, International Search Report and Written Opinion issued in PCT/US2021/041737, mailed on Oct. 28, 2021.

Levin et al., "Identification and Validation of T-cell Receptors Targeting RAS Hotspot Mutations in Human Cancers for Use in Cell-based Immunotherapy", *Clinical Cancer Research,* 27(18): 5084-5095 (2021).

Malekzadeh et al., "T cell receptor (TCR) alpha chain, SEQ ID 375", Database accession No. BGE46898, published May 16, 2019.

Riddell et al., "The use of anti-CD3 and anti-CD28 monoclonal antibodies to clone and expand human antigen-specific T cells", *Journal of Immunological Methods,* 128(2): 189-201 (1990).

Szymczak et al., "Correction of multi-gene deficiency in vivo using a single 'self-cleaving' 2A peptide-based retroviral vector", *Nature Biotechnology,* 22(5): 589-594 (2004).

Tran et al. "Cancer Immunotherapy Based on Mutation-Specific CD4+ T Cells in a Patient with Epithelial Cancer", *Science* 344(6184): 641-645 (2014).

Tran et al. "T-Cell Transfer Therapy Targeting Mutant KRAS in Cancer", *New England Journal of Medicine,* 375(23): 2255-2262 (2016).

Wang et. al. "Identification of T-cell Receptors Targeting KRAS-Mutated Human Tumors", *Cancer Immunology Research,* 4(3):204-14 (2016).

Murphy et al., eds., Janeway's Immunobiology, 7th Ed., New York: Garland Science (2008), pp. 157-158 (Section 4-10).

* cited by examiner

```
                          SEQUENCE LISTING

<160> NUMBER OF SEQ ID NOS: 40

<210> SEQ ID NO 1
<211> LENGTH: 6
<212> TYPE: PRT
<213> ORGANISM: Homo sapiens

<400> SEQUENCE: 1

Tyr Ser Gly Ser Pro Glu
1               5

<210> SEQ ID NO 2
<211> LENGTH: 4
<212> TYPE: PRT
<213> ORGANISM: Homo sapiens

<400> SEQUENCE: 2

His Ile Ser Arg
1

<210> SEQ ID NO 3
<211> LENGTH: 12
<212> TYPE: PRT
<213> ORGANISM: Homo sapiens

<400> SEQUENCE: 3

Cys Ala Leu Leu Gln Gly Ala Gln Lys Leu Val Phe
1               5                   10

<210> SEQ ID NO 4
<211> LENGTH: 5
<212> TYPE: PRT
<213> ORGANISM: Homo sapiens

<400> SEQUENCE: 4

Ser Gln Val Thr Met
1               5

<210> SEQ ID NO 5
<211> LENGTH: 7
<212> TYPE: PRT
<213> ORGANISM: Homo sapiens

<400> SEQUENCE: 5

Ala Asn Gln Gly Ser Glu Ala
1               5

<210> SEQ ID NO 6
<211> LENGTH: 13
<212> TYPE: PRT
<213> ORGANISM: Homo sapiens

<400> SEQUENCE: 6

Cys Ser Val Glu Ser Gly Gln Asp Tyr Gly Tyr Thr Phe
1               5                   10

<210> SEQ ID NO 7
<211> LENGTH: 108
<212> TYPE: PRT
```

<213> ORGANISM: Homo sapiens

<400> SEQUENCE: 7

```
Ala Gln Arg Val Thr Gln Pro Glu Lys Leu Leu Ser Val Phe Lys Gly
1               5                   10                  15

Ala Pro Val Glu Leu Lys Cys Asn Tyr Ser Tyr Ser Gly Ser Pro Glu
                20                  25                  30

Leu Phe Trp Tyr Val Gln Tyr Ser Arg Gln Arg Leu Gln Leu Leu Leu
            35                  40                  45

Arg His Ile Ser Arg Glu Ser Ile Lys Gly Phe Thr Ala Asp Leu Asn
        50                  55                  60

Lys Gly Glu Thr Ser Phe His Leu Lys Lys Pro Phe Ala Gln Glu Glu
65                  70                  75                  80

Asp Ser Ala Met Tyr Tyr Cys Ala Leu Leu Gln Gly Ala Gln Lys Leu
                85                  90                  95

Val Phe Gly Gln Gly Thr Arg Leu Thr Ile Asn Pro
                100                 105
```

<210> SEQ ID NO 8
<211> LENGTH: 114
<212> TYPE: PRT
<213> ORGANISM: Homo sapiens

<400> SEQUENCE: 8

```
Ser Ala Val Ile Ser Gln Lys Pro Ser Arg Asp Ile Cys Gln Arg Gly
1               5                   10                  15

Thr Ser Leu Thr Ile Gln Cys Gln Val Asp Ser Gln Val Thr Met Met
                20                  25                  30

Phe Trp Tyr Arg Gln Gln Pro Gly Gln Ser Leu Thr Leu Ile Ala Thr
            35                  40                  45

Ala Asn Gln Gly Ser Glu Ala Thr Tyr Glu Ser Gly Phe Val Ile Asp
        50                  55                  60

Lys Phe Pro Ile Ser Arg Pro Asn Leu Thr Phe Ser Thr Leu Thr Val
65                  70                  75                  80

Ser Asn Met Ser Pro Glu Asp Ser Ser Ile Tyr Leu Cys Ser Val Glu
                85                  90                  95

Ser Gly Gln Asp Tyr Gly Tyr Thr Phe Gly Ser Gly Thr Arg Leu Thr
                100                 105                 110

Val Val
```

<210> SEQ ID NO 9
<211> LENGTH: 127
<212> TYPE: PRT
<213> ORGANISM: Homo sapiens

<400> SEQUENCE: 9

```
Met Lys Pro Thr Leu Ile Ser Val Leu Val Ile Ile Phe Ile Leu Arg
1               5                   10                  15

Gly Thr Arg Ala Gln Arg Val Thr Gln Pro Glu Lys Leu Leu Ser Val
                20                  25                  30

Phe Lys Gly Ala Pro Val Glu Leu Lys Cys Asn Tyr Ser Tyr Ser Gly
            35                  40                  45

Ser Pro Glu Leu Phe Trp Tyr Val Gln Tyr Ser Arg Gln Arg Leu Gln
        50                  55                  60

Leu Leu Leu Arg His Ile Ser Arg Glu Ser Ile Lys Gly Phe Thr Ala
65                  70                  75                  80
```

-continued

Asp Leu Asn Lys Gly Glu Thr Ser Phe His Leu Lys Lys Pro Phe Ala
                85                  90                  95

Gln Glu Glu Asp Ser Ala Met Tyr Tyr Cys Ala Leu Leu Gln Gly Ala
            100                 105                 110

Gln Lys Leu Val Phe Gly Gln Gly Thr Arg Leu Thr Ile Asn Pro
        115                 120                 125

<210> SEQ ID NO 10
<211> LENGTH: 129
<212> TYPE: PRT
<213> ORGANISM: Homo sapiens

<400> SEQUENCE: 10

Met Ala Ser Leu Leu Leu Leu Leu Leu Gly Leu Gly Ser Val Phe Ser
1               5                   10                  15

Ala Val Ile Ser Gln Lys Pro Ser Arg Asp Ile Cys Gln Arg Gly Thr
            20                  25                  30

Ser Leu Thr Ile Gln Cys Gln Val Asp Ser Gln Val Thr Met Met Phe
        35                  40                  45

Trp Tyr Arg Gln Gln Pro Gly Gln Ser Leu Thr Leu Ile Ala Thr Ala
    50                  55                  60

Asn Gln Gly Ser Glu Ala Thr Tyr Glu Ser Gly Phe Val Ile Asp Lys
65                  70                  75                  80

Phe Pro Ile Ser Arg Pro Asn Leu Thr Phe Ser Thr Leu Thr Val Ser
                85                  90                  95

Asn Met Ser Pro Glu Asp Ser Ser Ile Tyr Leu Cys Ser Val Glu Ser
            100                 105                 110

Gly Gln Asp Tyr Gly Tyr Thr Phe Gly Ser Gly Thr Arg Leu Thr Val
        115                 120                 125

Val

<210> SEQ ID NO 11
<211> LENGTH: 189
<212> TYPE: PRT
<213> ORGANISM: Homo sapiens

<400> SEQUENCE: 11

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
    130                 135                 140

Ser Ala Lys Thr Arg Gln Arg Val Glu Asp Ala Phe Tyr Thr Leu Val

```
145                 150                 155                 160

Arg Glu Ile Arg Gln Tyr Arg Leu Lys Lys Ile Ser Lys Glu Glu Lys
                165                 170                 175

Thr Pro Gly Cys Val Lys Ile Lys Lys Cys Ile Ile Met
            180                 185

<210> SEQ ID NO 12
<211> LENGTH: 188
<212> TYPE: PRT
<213> ORGANISM: Homo sapiens

<400> SEQUENCE: 12

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
                20                  25                  30

Asp Pro Thr Ile Glu Asp Ser Tyr Arg Lys Gln Val Val Ile Asp Gly
            35                  40                  45

Glu Thr Cys Leu Leu Asp Ile Leu Asp Thr Ala Gly Gln Glu Glu Tyr
        50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
                100                 105                 110

Leu Val Gly Asn Lys Cys Asp Leu Pro Ser Arg Thr Val Asp Thr Lys
            115                 120                 125

Gln Ala Gln Asp Leu Ala Arg Ser Tyr Gly Ile Pro Phe Ile Glu Thr
        130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Lys Ser Lys Thr Lys Cys Val Ile Met
            180                 185

<210> SEQ ID NO 13
<211> LENGTH: 189
<212> TYPE: PRT
<213> ORGANISM: Homo sapiens

<400> SEQUENCE: 13

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
                20                  25                  30

Asp Pro Thr Ile Glu Asp Ser Tyr Arg Lys Gln Val Val Ile Asp Gly
            35                  40                  45

Glu Thr Cys Leu Leu Asp Ile Leu Asp Thr Ala Gly Gln Glu Glu Tyr
        50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His Gln Tyr
                85                  90                  95

Arg Glu Gln Ile Lys Arg Val Lys Asp Ser Asp Asp Val Pro Met Val
```

-continued

```
                100               105               110

Leu Val Gly Asn Lys Cys Asp Leu Ala Ala Arg Thr Val Glu Ser Arg
        115               120               125

Gln Ala Gln Asp Leu Ala Arg Ser Tyr Gly Ile Pro Tyr Ile Glu Thr
    130               135               140

Ser Ala Lys Thr Arg Gln Gly Val Glu Asp Ala Phe Tyr Thr Leu Val
145               150               155               160

Arg Glu Ile Arg Gln His Lys Leu Arg Lys Leu Asn Pro Pro Asp Glu
                165               170               175

Ser Gly Pro Gly Cys Met Ser Cys Lys Cys Val Leu Ser
            180               185

<210> SEQ ID NO 14
<211> LENGTH: 189
<212> TYPE: PRT
<213> ORGANISM: Homo sapiens

<400> SEQUENCE: 14

Met Thr Glu Tyr Lys Leu Val Val Val Gly Ala Gly Gly Val Gly Lys
1               5                 10                15

Ser Ala Leu Thr Ile Gln Leu Ile Gln Asn His Phe Val Asp Glu Tyr
            20                25                30

Asp Pro Thr Ile Glu Asp Ser Tyr Arg Lys Gln Val Val Ile Asp Gly
        35                40                45

Glu Thr Cys Leu Leu Asp Ile Leu Asp Thr Ala Gly Gln Glu Glu Tyr
    50                55                60

Ser Ala Met Arg Asp Gln Tyr Met Arg Thr Gly Glu Gly Phe Leu Cys
65                70                75                80

Val Phe Ala Ile Asn Asn Ser Lys Ser Phe Ala Asp Ile Asn Leu Tyr
                85                90                95

Arg Glu Gln Ile Lys Arg Val Lys Asp Ser Asp Asp Val Pro Met Val
            100               105               110

Leu Val Gly Asn Lys Cys Asp Leu Pro Thr Arg Thr Val Asp Thr Lys
        115               120               125

Gln Ala His Glu Leu Ala Lys Ser Tyr Gly Ile Pro Phe Ile Glu Thr
    130               135               140

Ser Ala Lys Thr Arg Gln Gly Val Glu Asp Ala Phe Tyr Thr Leu Val
145               150               155               160

Arg Glu Ile Arg Gln Tyr Arg Met Lys Lys Leu Asn Ser Ser Asp Asp
                165               170               175

Gly Thr Gln Gly Cys Met Gly Leu Pro Cys Val Val Met
            180               185

<210> SEQ ID NO 15
<211> LENGTH: 189
<212> TYPE: PRT
<213> ORGANISM: Homo sapiens

<400> SEQUENCE: 15

Met Thr Glu Tyr Lys Leu Val Val Val Gly Ala Val Gly Val Gly Lys
1               5                 10                15

Ser Ala Leu Thr Ile Gln Leu Ile Gln Asn His Phe Val Asp Glu Tyr
            20                25                30

Asp Pro Thr Ile Glu Asp Ser Tyr Arg Lys Gln Val Val Ile Asp Gly
        35                40                45

Glu Thr Cys Leu Leu Asp Ile Leu Asp Thr Ala Gly Gln Glu Glu Tyr
```

```
                50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
                100                 105                 110

Leu Val Gly Asn Lys Cys Asp Leu Pro Ser Arg Thr Val Asp Thr Lys
            115                 120                 125

Gln Ala Gln Asp Leu Ala Arg Ser Tyr Gly Ile Pro Phe Ile Glu Thr
        130                 135                 140

Ser Ala Lys Thr Arg Gln Arg Val Glu Asp Ala Phe Tyr Thr Leu Val
145                 150                 155                 160

Arg Glu Ile Arg Gln Tyr Arg Leu Lys Lys Ile Ser Lys Glu Glu Lys
                165                 170                 175

Thr Pro Gly Cys Val Lys Ile Lys Lys Cys Ile Ile Met
            180                 185

<210> SEQ ID NO 16
<211> LENGTH: 188
<212> TYPE: PRT
<213> ORGANISM: Homo sapiens

<400> SEQUENCE: 16

Met Thr Glu Tyr Lys Leu Val Val Val Gly Ala Val Gly Val Gly Lys
1               5                   10                  15

Ser Ala Leu Thr Ile Gln Leu Ile Gln Asn His Phe Val Asp Glu Tyr
                20                  25                  30

Asp Pro Thr Ile Glu Asp Ser Tyr Arg Lys Gln Val Val Ile Asp Gly
            35                  40                  45

Glu Thr Cys Leu Leu Asp Ile Leu Asp Thr Ala Gly Gln Glu Glu Tyr
        50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
                100                 105                 110

Leu Val Gly Asn Lys Cys Asp Leu Pro Ser Arg Thr Val Asp Thr Lys
            115                 120                 125

Gln Ala Gln Asp Leu Ala Arg Ser Tyr Gly Ile Pro Phe Ile Glu Thr
        130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Lys Ser Lys Thr Lys Cys Val Ile Met
            180                 185

<210> SEQ ID NO 17
<211> LENGTH: 189
<212> TYPE: PRT
<213> ORGANISM: Homo sapiens

<400> SEQUENCE: 17

Met Thr Glu Tyr Lys Leu Val Val Val Gly Ala Val Gly Val Gly Lys
```

-continued

```
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
            35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His Gln Tyr
                85                  90                  95

Arg Glu Gln Ile Lys Arg Val Lys Asp Ser Asp Asp Val Pro Met Val
                100                 105                 110

Leu Val Gly Asn Lys Cys Asp Leu Ala Ala Arg Thr Val Glu Ser Arg
                115                 120                 125

Gln Ala Gln Asp Leu Ala Arg Ser Tyr Gly Ile Pro Tyr Ile Glu Thr
    130                 135                 140

Ser Ala Lys Thr Arg Gln Gly Val Glu Asp Ala Phe Tyr Thr Leu Val
145                 150                 155                 160

Arg Glu Ile Arg Gln His Lys Leu Arg Lys Leu Asn Pro Pro Asp Glu
                165                 170                 175

Ser Gly Pro Gly Cys Met Ser Cys Lys Cys Val Leu Ser
            180                 185

<210> SEQ ID NO 18
<211> LENGTH: 189
<212> TYPE: PRT
<213> ORGANISM: Homo sapiens

<400> SEQUENCE: 18

Met Thr Glu Tyr Lys Leu Val Val Val Gly Ala Val Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
            35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Ser Lys Ser Phe Ala Asp Ile Asn Leu Tyr
                85                  90                  95

Arg Glu Gln Ile Lys Arg Val Lys Asp Ser Asp Asp Val Pro Met Val
                100                 105                 110

Leu Val Gly Asn Lys Cys Asp Leu Pro Thr Arg Thr Val Asp Thr Lys
                115                 120                 125

Gln Ala His Glu Leu Ala Lys Ser Tyr Gly Ile Pro Phe Ile Glu Thr
    130                 135                 140

Ser Ala Lys Thr Arg Gln Gly Val Glu Asp Ala Phe Tyr Thr Leu Val
145                 150                 155                 160

Arg Glu Ile Arg Gln Tyr Arg Met Lys Lys Leu Asn Ser Ser Asp Asp
                165                 170                 175

Gly Thr Gln Gly Cys Met Gly Leu Pro Cys Val Val Met
            180                 185
```

```
<210> SEQ ID NO 19
<211> LENGTH: 137
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (48)..(48)
<223> OTHER INFORMATION: X is Thr or Cys
<220> FEATURE:
<221> NAME/KEY: MISC_FEATURE
<222> LOCATION: (112)..(112)
<223> OTHER INFORMATION: X is Ser, Ala, Val, Leu, Ile, Pro, Phe, Met, or
     Trp
<220> FEATURE:
<221> NAME/KEY: MISC_FEATURE
<222> LOCATION: (114)..(114)
<223> OTHER INFORMATION: X is Met, Ala, Val, Leu, Ile, Pro, Phe, or Trp
<220> FEATURE:
<221> NAME/KEY: MISC_FEATURE
<222> LOCATION: (115)..(115)
<223> OTHER INFORMATION: X is Gly, Ala, Val, Leu, Ile, Pro, Phe, Met, or
     Trp

<400> SEQUENCE: 19

Asn Ile Gln Asn Pro Glu Pro Ala Val Tyr Gln Leu Lys Asp Pro Arg
1               5                   10                  15

Ser Gln Asp Ser Thr Leu Cys Leu Phe Thr Asp Phe Asp Ser Gln Ile
            20                  25                  30

Asn Val Pro Lys Thr Met Glu Ser Gly Thr Phe Ile Thr Asp Lys Xaa
        35                  40                  45

Val Leu Asp Met Lys Ala Met Asp Ser Lys Ser Asn Gly Ala Ile Ala
    50                  55                  60

Trp Ser Asn Gln Thr Ser Phe Thr Cys Gln Asp Ile Phe Lys Glu Thr
65                  70                  75                  80

Asn Ala Thr Tyr Pro Ser Ser Asp Val Pro Cys Asp Ala Thr Leu Thr
                85                  90                  95

Glu Lys Ser Phe Glu Thr Asp Met Asn Leu Asn Phe Gln Asn Leu Xaa
            100                 105                 110

Val Xaa Xaa Leu Arg Ile Leu Leu Leu Lys Val Ala Gly Phe Asn Leu
        115                 120                 125

Leu Met Thr Leu Arg Leu Trp Ser Ser
    130                 135

<210> SEQ ID NO 20
<211> LENGTH: 173
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (57)..(57)
<223> OTHER INFORMATION: X is Ser or Cys

<400> SEQUENCE: 20

Glu Asp Leu Arg Asn Val Thr Pro Pro Lys Val Ser Leu Phe Glu Pro
1               5                   10                  15

Ser Lys Ala Glu Ile Ala Asn Lys Gln Lys Ala Thr Leu Val Cys Leu
            20                  25                  30

Ala Arg Gly Phe Phe Pro Asp His Val Glu Leu Ser Trp Trp Val Asn
        35                  40                  45

Gly Lys Glu Val His Ser Gly Val Xaa Thr Asp Pro Gln Ala Tyr Lys
```

```
        50              55              60

Glu Ser Asn Tyr Ser Tyr Cys Leu Ser Ser Arg Leu Arg Val Ser Ala
65              70              75              80

Thr Phe Trp His Asn Pro Arg Asn His Phe Arg Cys Gln Val Gln Phe
            85              90              95

His Gly Leu Ser Glu Glu Asp Lys Trp Pro Glu Gly Ser Pro Lys Pro
            100             105             110

Val Thr Gln Asn Ile Ser Ala Glu Ala Trp Gly Arg Ala Asp Cys Gly
        115             120             125

Ile Thr Ser Ala Ser Tyr Gln Gln Gly Val Leu Ser Ala Thr Ile Leu
        130             135             140

Tyr Glu Ile Leu Leu Gly Lys Ala Thr Leu Tyr Ala Val Leu Val Ser
145             150             155             160

Thr Leu Val Val Met Ala Met Val Lys Arg Lys Asn Ser
            165             170

<210> SEQ ID NO 21
<211> LENGTH: 137
<212> TYPE: PRT
<213> ORGANISM: Artificial Sequence
<220> FEATURE:
<223> OTHER INFORMATION: Synthetic

<400> SEQUENCE: 21

Asn Ile Gln Asn Pro Glu Pro Ala Val Tyr Gln Leu Lys Asp Pro Arg
1               5               10              15

Ser Gln Asp Ser Thr Leu Cys Leu Phe Thr Asp Phe Asp Ser Gln Ile
            20              25              30

Asn Val Pro Lys Thr Met Glu Ser Gly Thr Phe Ile Thr Asp Lys Cys
        35              40              45

Val Leu Asp Met Lys Ala Met Asp Ser Lys Ser Asn Gly Ala Ile Ala
        50              55              60

Trp Ser Asn Gln Thr Ser Phe Thr Cys Gln Asp Ile Phe Lys Glu Thr
65              70              75              80

Asn Ala Thr Tyr Pro Ser Ser Asp Val Pro Cys Asp Ala Thr Leu Thr
            85              90              95

Glu Lys Ser Phe Glu Thr Asp Met Asn Leu Asn Phe Gln Asn Leu Leu
            100             105             110

Val Ile Val Leu Arg Ile Leu Leu Leu Lys Val Ala Gly Phe Asn Leu
        115             120             125

Leu Met Thr Leu Arg Leu Trp Ser Ser
        130             135

<210> SEQ ID NO 22
<211> LENGTH: 173
<212> TYPE: PRT
<213> ORGANISM: Artificial Sequence
<220> FEATURE:
<223> OTHER INFORMATION: Synthetic

<400> SEQUENCE: 22

Glu Asp Leu Arg Asn Val Thr Pro Pro Lys Val Ser Leu Phe Glu Pro
1               5               10              15

Ser Lys Ala Glu Ile Ala Asn Lys Gln Lys Ala Thr Leu Val Cys Leu
            20              25              30

Ala Arg Gly Phe Phe Pro Asp His Val Glu Leu Ser Trp Trp Val Asn
        35              40              45
```

-continued

```
Gly Lys Glu Val His Ser Gly Val Cys Thr Asp Pro Gln Ala Tyr Lys
    50              55              60

Glu Ser Asn Tyr Ser Tyr Cys Leu Ser Ser Arg Leu Arg Val Ser Ala
65              70              75              80

Thr Phe Trp His Asn Pro Arg Asn His Phe Arg Cys Gln Val Gln Phe
                85              90              95

His Gly Leu Ser Glu Glu Asp Lys Trp Pro Glu Gly Ser Pro Lys Pro
            100             105             110

Val Thr Gln Asn Ile Ser Ala Glu Ala Trp Gly Arg Ala Asp Cys Gly
            115             120             125

Ile Thr Ser Ala Ser Tyr Gln Gln Gly Val Leu Ser Ala Thr Ile Leu
    130             135             140

Tyr Glu Ile Leu Leu Gly Lys Ala Thr Leu Tyr Ala Val Leu Val Ser
145             150             155             160

Thr Leu Val Val Met Ala Met Val Lys Arg Lys Asn Ser
                165             170
```

```
<210> SEQ ID NO 23
<211> LENGTH: 137
<212> TYPE: PRT
<213> ORGANISM: Mus musculus

<400> SEQUENCE: 23
```

```
Asn Ile Gln Asn Pro Glu Pro Ala Val Tyr Gln Leu Lys Asp Pro Arg
1               5               10              15

Ser Gln Asp Ser Thr Leu Cys Leu Phe Thr Asp Phe Asp Ser Gln Ile
            20              25              30

Asn Val Pro Lys Thr Met Glu Ser Gly Thr Phe Ile Thr Asp Lys Thr
        35              40              45

Val Leu Asp Met Lys Ala Met Asp Ser Lys Ser Asn Gly Ala Ile Ala
    50              55              60

Trp Ser Asn Gln Thr Ser Phe Thr Cys Gln Asp Ile Phe Lys Glu Thr
65              70              75              80

Asn Ala Thr Tyr Pro Ser Ser Asp Val Pro Cys Asp Ala Thr Leu Thr
                85              90              95

Glu Lys Ser Phe Glu Thr Asp Met Asn Leu Asn Phe Gln Asn Leu Ser
            100             105             110

Val Met Gly Leu Arg Ile Leu Leu Leu Lys Val Ala Gly Phe Asn Leu
            115             120             125

Leu Met Thr Leu Arg Leu Trp Ser Ser
    130             135
```

```
<210> SEQ ID NO 24
<211> LENGTH: 173
<212> TYPE: PRT
<213> ORGANISM: Mus musculus

<400> SEQUENCE: 24
```

```
Glu Asp Leu Arg Asn Val Thr Pro Pro Lys Val Ser Leu Phe Glu Pro
1               5               10              15

Ser Lys Ala Glu Ile Ala Asn Lys Gln Lys Ala Thr Leu Val Cys Leu
            20              25              30

Ala Arg Gly Phe Phe Pro Asp His Val Glu Leu Ser Trp Trp Val Asn
        35              40              45

Gly Lys Glu Val His Ser Gly Val Ser Thr Asp Pro Gln Ala Tyr Lys
    50              55              60
```

```
Glu Ser Asn Tyr Ser Tyr Cys Leu Ser Ser Arg Leu Arg Val Ser Ala
65              70                  75                  80

Thr Phe Trp His Asn Pro Arg Asn His Phe Arg Cys Gln Val Gln Phe
                85                  90                  95

His Gly Leu Ser Glu Glu Asp Lys Trp Pro Glu Gly Ser Pro Lys Pro
                100                 105                 110

Val Thr Gln Asn Ile Ser Ala Glu Ala Trp Gly Arg Ala Asp Cys Gly
        115                 120                 125

Ile Thr Ser Ala Ser Tyr Gln Gln Gly Val Leu Ser Ala Thr Ile Leu
        130                 135                 140

Tyr Glu Ile Leu Leu Gly Lys Ala Thr Leu Tyr Ala Val Leu Val Ser
145                 150                 155                 160

Thr Leu Val Val Met Ala Met Val Lys Arg Lys Asn Ser
                165                 170
```

```
<210> SEQ ID NO 25
<211> LENGTH: 264
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (175)..(175)
<223> OTHER INFORMATION: X is Thr or Cys
<220> FEATURE:
<221> NAME/KEY: MISC_FEATURE
<222> LOCATION: (239)..(239)
<223> OTHER INFORMATION: X is Ser, Ala, Val, Leu, Ile, Pro, Phe, Met, or
     Trp
<220> FEATURE:
<221> NAME/KEY: MISC_FEATURE
<222> LOCATION: (241)..(241)
<223> OTHER INFORMATION: X is Met, Ala, Val, Leu, Ile, Pro, Phe, or Trp
<220> FEATURE:
<221> NAME/KEY: MISC_FEATURE
<222> LOCATION: (242)..(242)
<223> OTHER INFORMATION: X is Gly, Ala, Val, Leu, Ile, Pro, Phe, Met, or
     Trp
```

```
<400> SEQUENCE: 25

Met Lys Pro Thr Leu Ile Ser Val Leu Val Ile Ile Phe Ile Leu Arg
1               5                   10                  15

Gly Thr Arg Ala Gln Arg Val Thr Gln Pro Glu Lys Leu Leu Ser Val
                20                  25                  30

Phe Lys Gly Ala Pro Val Glu Leu Lys Cys Asn Tyr Ser Tyr Ser Gly
            35                  40                  45

Ser Pro Glu Leu Phe Trp Tyr Val Gln Tyr Ser Arg Gln Arg Leu Gln
        50                  55                  60

Leu Leu Leu Arg His Ile Ser Arg Glu Ser Ile Lys Gly Phe Thr Ala
65                  70                  75                  80

Asp Leu Asn Lys Gly Glu Thr Ser Phe His Leu Lys Lys Pro Phe Ala
                85                  90                  95

Gln Glu Glu Asp Ser Ala Met Tyr Tyr Cys Ala Leu Leu Gln Gly Ala
                100                 105                 110

Gln Lys Leu Val Phe Gly Gln Gly Thr Arg Leu Thr Ile Asn Pro Asn
        115                 120                 125

Ile Gln Asn Pro Glu Pro Ala Val Tyr Gln Leu Lys Asp Pro Arg Ser
        130                 135                 140

Gln Asp Ser Thr Leu Cys Leu Phe Thr Asp Phe Asp Ser Gln Ile Asn
145                 150                 155                 160
```

-continued

```
Val Pro Lys Thr Met Glu Ser Gly Thr Phe Ile Thr Asp Lys Xaa Val
                165                 170                 175

Leu Asp Met Lys Ala Met Asp Ser Lys Ser Asn Gly Ala Ile Ala Trp
            180                 185                 190

Ser Asn Gln Thr Ser Phe Thr Cys Gln Asp Ile Phe Lys Glu Thr Asn
        195                 200                 205

Ala Thr Tyr Pro Ser Ser Asp Val Pro Cys Asp Ala Thr Leu Thr Glu
    210                 215                 220

Lys Ser Phe Glu Thr Asp Met Asn Leu Asn Phe Gln Asn Leu Xaa Val
225                 230                 235                 240

Xaa Xaa Leu Arg Ile Leu Leu Leu Lys Val Ala Gly Phe Asn Leu Leu
            245                 250                 255

Met Thr Leu Arg Leu Trp Ser Ser
            260

<210> SEQ ID NO 26
<211> LENGTH: 302
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (186)..(186)
<223> OTHER INFORMATION: X is Ser or Cys

<400> SEQUENCE: 26

Met Ala Ser Leu Leu Leu Leu Leu Leu Gly Leu Gly Ser Val Phe Ser
1               5                   10                  15

Ala Val Ile Ser Gln Lys Pro Ser Arg Asp Ile Cys Gln Arg Gly Thr
            20                  25                  30

Ser Leu Thr Ile Gln Cys Gln Val Asp Ser Gln Val Thr Met Met Phe
        35                  40                  45

Trp Tyr Arg Gln Gln Pro Gly Gln Ser Leu Thr Leu Ile Ala Thr Ala
    50                  55                  60

Asn Gln Gly Ser Glu Ala Thr Tyr Glu Ser Gly Phe Val Ile Asp Lys
65                  70                  75                  80

Phe Pro Ile Ser Arg Pro Asn Leu Thr Phe Ser Thr Leu Thr Val Ser
            85                  90                  95

Asn Met Ser Pro Glu Asp Ser Ser Ile Tyr Leu Cys Ser Val Glu Ser
            100                 105                 110

Gly Gln Asp Tyr Gly Tyr Thr Phe Gly Ser Gly Thr Arg Leu Thr Val
        115                 120                 125

Val Glu Asp Leu Arg Asn Val Thr Pro Pro Lys Val Ser Leu Phe Glu
    130                 135                 140

Pro Ser Lys Ala Glu Ile Ala Asn Lys Gln Lys Ala Thr Leu Val Cys
145                 150                 155                 160

Leu Ala Arg Gly Phe Phe Pro Asp His Val Glu Leu Ser Trp Trp Val
            165                 170                 175

Asn Gly Lys Glu Val His Ser Gly Val Xaa Thr Asp Pro Gln Ala Tyr
            180                 185                 190

Lys Glu Ser Asn Tyr Ser Tyr Cys Leu Ser Ser Arg Leu Arg Val Ser
        195                 200                 205

Ala Thr Phe Trp His Asn Pro Arg Asn His Phe Arg Cys Gln Val Gln
    210                 215                 220

Phe His Gly Leu Ser Glu Glu Asp Lys Trp Pro Glu Gly Ser Pro Lys
225                 230                 235                 240
```

```
Pro Val Thr Gln Asn Ile Ser Ala Glu Ala Trp Gly Arg Ala Asp Cys
            245                 250                 255

Gly Ile Thr Ser Ala Ser Tyr Gln Gln Gly Val Leu Ser Ala Thr Ile
            260                 265                 270

Leu Tyr Glu Ile Leu Leu Gly Lys Ala Thr Leu Tyr Ala Val Leu Val
        275                 280                 285

Ser Thr Leu Val Val Met Ala Met Val Lys Arg Lys Asn Ser
    290                 295                 300
```

```
<210> SEQ ID NO 27
<211> LENGTH: 245
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (156)..(156)
<223> OTHER INFORMATION: X is Thr or Cys
<220> FEATURE:
<221> NAME/KEY: MISC_FEATURE
<222> LOCATION: (220)..(220)
<223> OTHER INFORMATION: X is Ser, Ala, Val, Leu, Ile, Pro, Phe, Met, or
      Trp
<220> FEATURE:
<221> NAME/KEY: MISC_FEATURE
<222> LOCATION: (222)..(222)
<223> OTHER INFORMATION: X is Met, Ala, Val, Leu, Ile, Pro, Phe, or Trp
<220> FEATURE:
<221> NAME/KEY: MISC_FEATURE
<222> LOCATION: (223)..(223)
<223> OTHER INFORMATION: X is Gly, Ala, Val, Leu, Ile, Pro, Phe, Met, or
      Trp

<400> SEQUENCE: 27
```

```
Ala Gln Arg Val Thr Gln Pro Glu Lys Leu Leu Ser Val Phe Lys Gly
1               5                   10                  15

Ala Pro Val Glu Leu Lys Cys Asn Tyr Ser Tyr Ser Gly Ser Pro Glu
            20                  25                  30

Leu Phe Trp Tyr Val Gln Tyr Ser Arg Gln Arg Leu Gln Leu Leu Leu
        35                  40                  45

Arg His Ile Ser Arg Glu Ser Ile Lys Gly Phe Thr Ala Asp Leu Asn
    50                  55                  60

Lys Gly Glu Thr Ser Phe His Leu Lys Lys Pro Phe Ala Gln Glu Glu
65                  70                  75                  80

Asp Ser Ala Met Tyr Tyr Cys Ala Leu Leu Gln Gly Ala Gln Lys Leu
            85                  90                  95

Val Phe Gly Gln Gly Thr Arg Leu Thr Ile Asn Pro Asn Ile Gln Asn
            100                 105                 110

Pro Glu Pro Ala Val Tyr Gln Leu Lys Asp Pro Arg Ser Gln Asp Ser
        115                 120                 125

Thr Leu Cys Leu Phe Thr Asp Phe Asp Ser Gln Ile Asn Val Pro Lys
    130                 135                 140

Thr Met Glu Ser Gly Thr Phe Ile Thr Asp Lys Xaa Val Leu Asp Met
145                 150                 155                 160

Lys Ala Met Asp Ser Lys Ser Asn Gly Ala Ile Ala Trp Ser Asn Gln
            165                 170                 175

Thr Ser Phe Thr Cys Gln Asp Ile Phe Lys Glu Thr Asn Ala Thr Tyr
            180                 185                 190

Pro Ser Ser Asp Val Pro Cys Asp Ala Thr Leu Thr Glu Lys Ser Phe
        195                 200                 205
```

Glu Thr Asp Met Asn Leu Asn Phe Gln Asn Leu Xaa Val Xaa Xaa Leu
    210                 215                 220

Arg Ile Leu Leu Leu Lys Val Ala Gly Phe Asn Leu Leu Met Thr Leu
225                 230                 235                 240

Arg Leu Trp Ser Ser
                245

<210> SEQ ID NO 28
<211> LENGTH: 287
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (171)..(171)
<223> OTHER INFORMATION: X is Ser or Cys

<400> SEQUENCE: 28

Ser Ala Val Ile Ser Gln Lys Pro Ser Arg Asp Ile Cys Gln Arg Gly
1               5                   10                  15

Thr Ser Leu Thr Ile Gln Cys Gln Val Asp Ser Gln Val Thr Met Met
            20                  25                  30

Phe Trp Tyr Arg Gln Gln Pro Gly Gln Ser Leu Thr Leu Ile Ala Thr
        35                  40                  45

Ala Asn Gln Gly Ser Glu Ala Thr Tyr Glu Ser Gly Phe Val Ile Asp
    50                  55                  60

Lys Phe Pro Ile Ser Arg Pro Asn Leu Thr Phe Ser Thr Leu Thr Val
65                  70                  75                  80

Ser Asn Met Ser Pro Glu Asp Ser Ser Ile Tyr Leu Cys Ser Val Glu
            85                  90                  95

Ser Gly Gln Asp Tyr Gly Tyr Thr Phe Gly Ser Gly Thr Arg Leu Thr
            100                 105                 110

Val Val Glu Asp Leu Arg Asn Val Thr Pro Pro Lys Val Ser Leu Phe
            115                 120                 125

Glu Pro Ser Lys Ala Glu Ile Ala Asn Lys Gln Lys Ala Thr Leu Val
    130                 135                 140

Cys Leu Ala Arg Gly Phe Phe Pro Asp His Val Glu Leu Ser Trp Trp
145                 150                 155                 160

Val Asn Gly Lys Glu Val His Ser Gly Val Xaa Thr Asp Pro Gln Ala
            165                 170                 175

Tyr Lys Glu Ser Asn Tyr Ser Tyr Cys Leu Ser Ser Arg Leu Arg Val
            180                 185                 190

Ser Ala Thr Phe Trp His Asn Pro Arg Asn His Phe Arg Cys Gln Val
            195                 200                 205

Gln Phe His Gly Leu Ser Glu Glu Asp Lys Trp Pro Glu Gly Ser Pro
    210                 215                 220

Lys Pro Val Thr Gln Asn Ile Ser Ala Glu Ala Trp Gly Arg Ala Asp
225                 230                 235                 240

Cys Gly Ile Thr Ser Ala Ser Tyr Gln Gln Gly Val Leu Ser Ala Thr
            245                 250                 255

Ile Leu Tyr Glu Ile Leu Leu Gly Lys Ala Thr Leu Tyr Ala Val Leu
            260                 265                 270

Val Ser Thr Leu Val Val Met Ala Met Val Lys Arg Lys Asn Ser
            275                 280                 285

-continued

```
<210> SEQ ID NO 29
<211> LENGTH: 264
<212> TYPE: PRT
<213> ORGANISM: Artificial Sequence
<220> FEATURE:
<223> OTHER INFORMATION: Synthetic

<400> SEQUENCE: 29

Met Lys Pro Thr Leu Ile Ser Val Leu Val Ile Ile Phe Ile Leu Arg
1               5                   10                  15

Gly Thr Arg Ala Gln Arg Val Thr Gln Pro Glu Lys Leu Leu Ser Val
            20                  25                  30

Phe Lys Gly Ala Pro Val Glu Leu Lys Cys Asn Tyr Ser Tyr Ser Gly
        35                  40                  45

Ser Pro Glu Leu Phe Trp Tyr Val Gln Tyr Ser Arg Gln Arg Leu Gln
    50                  55                  60

Leu Leu Leu Arg His Ile Ser Arg Glu Ser Ile Lys Gly Phe Thr Ala
65                  70                  75                  80

Asp Leu Asn Lys Gly Glu Thr Ser Phe His Leu Lys Lys Pro Phe Ala
                85                  90                  95

Gln Glu Glu Asp Ser Ala Met Tyr Tyr Cys Ala Leu Leu Gln Gly Ala
            100                 105                 110

Gln Lys Leu Val Phe Gly Gln Gly Thr Arg Leu Thr Ile Asn Pro Asn
        115                 120                 125

Ile Gln Asn Pro Glu Pro Ala Val Tyr Gln Leu Lys Asp Pro Arg Ser
    130                 135                 140

Gln Asp Ser Thr Leu Cys Leu Phe Thr Asp Phe Asp Ser Gln Ile Asn
145                 150                 155                 160

Val Pro Lys Thr Met Glu Ser Gly Thr Phe Ile Thr Asp Lys Cys Val
                165                 170                 175

Leu Asp Met Lys Ala Met Asp Ser Lys Ser Asn Gly Ala Ile Ala Trp
            180                 185                 190

Ser Asn Gln Thr Ser Phe Thr Cys Gln Asp Ile Phe Lys Glu Thr Asn
        195                 200                 205

Ala Thr Tyr Pro Ser Ser Asp Val Pro Cys Asp Ala Thr Leu Thr Glu
    210                 215                 220

Lys Ser Phe Glu Thr Asp Met Asn Leu Asn Phe Gln Asn Leu Leu Val
225                 230                 235                 240

Ile Val Leu Arg Ile Leu Leu Leu Lys Val Ala Gly Phe Asn Leu Leu
                245                 250                 255

Met Thr Leu Arg Leu Trp Ser Ser
            260

<210> SEQ ID NO 30
<211> LENGTH: 302
<212> TYPE: PRT
<213> ORGANISM: Artificial Sequence
<220> FEATURE:
<223> OTHER INFORMATION: Synthetic

<400> SEQUENCE: 30

Met Ala Ser Leu Leu Leu Leu Leu Leu Gly Leu Gly Ser Val Phe Ser
1               5                   10                  15

Ala Val Ile Ser Gln Lys Pro Ser Arg Asp Ile Cys Gln Arg Gly Thr
            20                  25                  30

Ser Leu Thr Ile Gln Cys Gln Val Asp Ser Gln Val Thr Met Met Phe
        35                  40                  45
```

```
Trp Tyr Arg Gln Gln Pro Gly Gln Ser Leu Thr Leu Ile Ala Thr Ala
    50              55                  60

Asn Gln Gly Ser Glu Ala Thr Tyr Glu Ser Gly Phe Val Ile Asp Lys
65              70                  75                  80

Phe Pro Ile Ser Arg Pro Asn Leu Thr Phe Ser Thr Leu Thr Val Ser
                85                  90                  95

Asn Met Ser Pro Glu Asp Ser Ser Ile Tyr Leu Cys Ser Val Glu Ser
                100                 105                 110

Gly Gln Asp Tyr Gly Tyr Thr Phe Gly Ser Gly Thr Arg Leu Thr Val
                115                 120                 125

Val Glu Asp Leu Arg Asn Val Thr Pro Pro Lys Val Ser Leu Phe Glu
                130                 135                 140

Pro Ser Lys Ala Glu Ile Ala Asn Lys Gln Lys Ala Thr Leu Val Cys
145                 150                 155                 160

Leu Ala Arg Gly Phe Phe Pro Asp His Val Glu Leu Ser Trp Trp Val
                165                 170                 175

Asn Gly Lys Glu Val His Ser Gly Val Cys Thr Asp Pro Gln Ala Tyr
                180                 185                 190

Lys Glu Ser Asn Tyr Ser Tyr Cys Leu Ser Ser Arg Leu Arg Val Ser
                195                 200                 205

Ala Thr Phe Trp His Asn Pro Arg Asn His Phe Arg Cys Gln Val Gln
    210                 215                 220

Phe His Gly Leu Ser Glu Glu Asp Lys Trp Pro Glu Gly Ser Pro Lys
225                 230                 235                 240

Pro Val Thr Gln Asn Ile Ser Ala Glu Ala Trp Gly Arg Ala Asp Cys
                245                 250                 255

Gly Ile Thr Ser Ala Ser Tyr Gln Gln Gly Val Leu Ser Ala Thr Ile
                260                 265                 270

Leu Tyr Glu Ile Leu Leu Gly Lys Ala Thr Leu Tyr Ala Val Leu Val
                275                 280                 285

Ser Thr Leu Val Val Met Ala Met Val Lys Arg Lys Asn Ser
    290                 295                 300
```

<210> SEQ ID NO 31
<211> LENGTH: 245
<212> TYPE: PRT
<213> ORGANISM: Artificial Sequence
<220> FEATURE:
<223> OTHER INFORMATION: Synthetic

<400> SEQUENCE: 31

```
Ala Gln Arg Val Thr Gln Pro Glu Lys Leu Leu Ser Val Phe Lys Gly
1               5                   10                  15

Ala Pro Val Glu Leu Lys Cys Asn Tyr Ser Tyr Ser Gly Ser Pro Glu
                20                  25                  30

Leu Phe Trp Tyr Val Gln Tyr Ser Arg Gln Arg Leu Gln Leu Leu Leu
        35                  40                  45

Arg His Ile Ser Arg Glu Ser Ile Lys Gly Phe Thr Ala Asp Leu Asn
    50                  55                  60

Lys Gly Glu Thr Ser Phe His Leu Lys Lys Pro Phe Ala Gln Glu Glu
65              70                  75                  80

Asp Ser Ala Met Tyr Tyr Cys Ala Leu Leu Gln Gly Ala Gln Lys Leu
                85                  90                  95

Val Phe Gly Gln Gly Thr Arg Leu Thr Ile Asn Pro Asn Ile Gln Asn
                100                 105                 110
```

-continued

```
Pro Glu Pro Ala Val Tyr Gln Leu Lys Asp Pro Arg Ser Gln Asp Ser
        115                 120                 125

Thr Leu Cys Leu Phe Thr Asp Phe Asp Ser Gln Ile Asn Val Pro Lys
    130                 135                 140

Thr Met Glu Ser Gly Thr Phe Ile Thr Asp Lys Cys Val Leu Asp Met
145                 150                 155                 160

Lys Ala Met Asp Ser Lys Ser Asn Gly Ala Ile Ala Trp Ser Asn Gln
                165                 170                 175

Thr Ser Phe Thr Cys Gln Asp Ile Phe Lys Glu Thr Asn Ala Thr Tyr
            180                 185                 190

Pro Ser Ser Asp Val Pro Cys Asp Ala Thr Leu Thr Glu Lys Ser Phe
            195                 200                 205

Glu Thr Asp Met Asn Leu Asn Phe Gln Asn Leu Leu Val Ile Val Leu
    210                 215                 220

Arg Ile Leu Leu Leu Lys Val Ala Gly Phe Asn Leu Leu Met Thr Leu
225                 230                 235                 240

Arg Leu Trp Ser Ser
                245

<210> SEQ ID NO 32
<211> LENGTH: 287
<212> TYPE: PRT
<213> ORGANISM: Artificial Sequence
<220> FEATURE:
<223> OTHER INFORMATION: Synthetic

<400> SEQUENCE: 32

Ser Ala Val Ile Ser Gln Lys Pro Ser Arg Asp Ile Cys Gln Arg Gly
1               5                   10                  15

Thr Ser Leu Thr Ile Gln Cys Gln Val Asp Ser Gln Val Thr Met Met
            20                  25                  30

Phe Trp Tyr Arg Gln Gln Pro Gly Gln Ser Leu Thr Leu Ile Ala Thr
            35                  40                  45

Ala Asn Gln Gly Ser Glu Ala Thr Tyr Glu Ser Gly Phe Val Ile Asp
    50                  55                  60

Lys Phe Pro Ile Ser Arg Pro Asn Leu Thr Phe Ser Thr Leu Thr Val
65                  70                  75                  80

Ser Asn Met Ser Pro Glu Asp Ser Ser Ile Tyr Leu Cys Ser Val Glu
                85                  90                  95

Ser Gly Gln Asp Tyr Gly Tyr Thr Phe Gly Ser Gly Thr Arg Leu Thr
            100                 105                 110

Val Val Glu Asp Leu Arg Asn Val Thr Pro Pro Lys Val Ser Leu Phe
        115                 120                 125

Glu Pro Ser Lys Ala Glu Ile Ala Asn Lys Gln Lys Ala Thr Leu Val
    130                 135                 140

Cys Leu Ala Arg Gly Phe Phe Pro Asp His Val Glu Leu Ser Trp Trp
145                 150                 155                 160

Val Asn Gly Lys Glu Val His Ser Gly Val Cys Thr Asp Pro Gln Ala
                165                 170                 175

Tyr Lys Glu Ser Asn Tyr Ser Tyr Cys Leu Ser Ser Arg Leu Arg Val
                180                 185                 190

Ser Ala Thr Phe Trp His Asn Pro Arg Asn His Phe Arg Cys Gln Val
            195                 200                 205

Gln Phe His Gly Leu Ser Glu Glu Asp Lys Trp Pro Glu Gly Ser Pro
    210                 215                 220
```

```
Lys Pro Val Thr Gln Asn Ile Ser Ala Glu Ala Trp Gly Arg Ala Asp
225             230                 235                 240

Cys Gly Ile Thr Ser Ala Ser Tyr Gln Gln Gly Val Leu Ser Ala Thr
            245                 250                 255

Ile Leu Tyr Glu Ile Leu Leu Gly Lys Ala Thr Leu Tyr Ala Val Leu
            260                 265                 270

Val Ser Thr Leu Val Val Met Ala Met Val Lys Arg Lys Asn Ser
        275                 280                 285
```

```
<210> SEQ ID NO 33
<211> LENGTH: 27
<212> TYPE: PRT
<213> ORGANISM: Artificial Sequence
<220> FEATURE:
<223> OTHER INFORMATION: Synthetic

<400> SEQUENCE: 33

Arg Ala Lys Arg Ser Gly Ser Gly Ala Thr Asn Phe Ser Leu Leu Lys
1               5                   10                  15

Gln Ala Gly Asp Val Glu Glu Asn Pro Gly Pro
            20                  25
```

```
<210> SEQ ID NO 34
<211> LENGTH: 24
<212> TYPE: PRT
<213> ORGANISM: Homo sapiens

<400> SEQUENCE: 34

Met Thr Glu Tyr Lys Leu Val Val Val Gly Ala Val Gly Val Gly Lys
1               5                   10                  15

Ser Ala Leu Thr Ile Gln Leu Ile
            20
```

```
<210> SEQ ID NO 35
<211> LENGTH: 24
<212> TYPE: PRT
<213> ORGANISM: Homo sapiens

<400> SEQUENCE: 35

Met Thr Glu Tyr Lys Leu Val Val Val Gly Ala Gly Gly Val Gly Lys
1               5                   10                  15

Ser Ala Leu Thr Ile Gln Leu Ile
            20
```

```
<210> SEQ ID NO 36
<211> LENGTH: 23
<212> TYPE: PRT
<213> ORGANISM: Homo sapiens

<400> SEQUENCE: 36

Thr Glu Tyr Lys Leu Val Val Val Gly Ala Gly Gly Val Gly Lys Ser
1               5                   10                  15

Ala Leu Thr Ile Gln Leu Ile
            20
```

```
<210> SEQ ID NO 37
<211> LENGTH: 593
<212> TYPE: PRT
<213> ORGANISM: Artificial Sequence
<220> FEATURE:
<223> OTHER INFORMATION: Synthetic

<400> SEQUENCE: 37
```

-continued

```
Met Ala Ser Leu Leu Leu Leu Leu Leu Gly Leu Gly Ser Val Phe Ser
1               5                   10                  15

Ala Val Ile Ser Gln Lys Pro Ser Arg Asp Ile Cys Gln Arg Gly Thr
            20                  25                  30

Ser Leu Thr Ile Gln Cys Gln Val Asp Ser Gln Val Thr Met Met Phe
            35                  40                  45

Trp Tyr Arg Gln Gln Pro Gly Gln Ser Leu Thr Leu Ile Ala Thr Ala
        50                  55                  60

Asn Gln Gly Ser Glu Ala Thr Tyr Glu Ser Gly Phe Val Ile Asp Lys
65                  70                  75                  80

Phe Pro Ile Ser Arg Pro Asn Leu Thr Phe Ser Thr Leu Thr Val Ser
                85                  90                  95

Asn Met Ser Pro Glu Asp Ser Ser Ile Tyr Leu Cys Ser Val Glu Ser
            100                 105                 110

Gly Gln Asp Tyr Gly Tyr Thr Phe Gly Ser Gly Thr Arg Leu Thr Val
            115                 120                 125

Val Glu Asp Leu Arg Asn Val Thr Pro Pro Lys Val Ser Leu Phe Glu
    130                 135                 140

Pro Ser Lys Ala Glu Ile Ala Asn Lys Gln Lys Ala Thr Leu Val Cys
145                 150                 155                 160

Leu Ala Arg Gly Phe Phe Pro Asp His Val Glu Leu Ser Trp Trp Val
                165                 170                 175

Asn Gly Lys Glu Val His Ser Gly Val Cys Thr Asp Pro Gln Ala Tyr
            180                 185                 190

Lys Glu Ser Asn Tyr Ser Tyr Cys Leu Ser Ser Arg Leu Arg Val Ser
            195                 200                 205

Ala Thr Phe Trp His Asn Pro Arg Asn His Phe Arg Cys Gln Val Gln
    210                 215                 220

Phe His Gly Leu Ser Glu Glu Asp Lys Trp Pro Glu Gly Ser Pro Lys
225                 230                 235                 240

Pro Val Thr Gln Asn Ile Ser Ala Glu Ala Trp Gly Arg Ala Asp Cys
                245                 250                 255

Gly Ile Thr Ser Ala Ser Tyr Gln Gln Gly Val Leu Ser Ala Thr Ile
            260                 265                 270

Leu Tyr Glu Ile Leu Leu Gly Lys Ala Thr Leu Tyr Ala Val Leu Val
        275                 280                 285

Ser Thr Leu Val Val Met Ala Met Val Lys Arg Lys Asn Ser Arg Ala
    290                 295                 300

Lys Arg Ser Gly Ser Gly Ala Thr Asn Phe Ser Leu Leu Lys Gln Ala
305                 310                 315                 320

Gly Asp Val Glu Glu Asn Pro Gly Pro Met Lys Pro Thr Leu Ile Ser
            325                 330                 335

Val Leu Val Ile Ile Phe Ile Leu Arg Gly Thr Arg Ala Gln Arg Val
            340                 345                 350

Thr Gln Pro Glu Lys Leu Leu Ser Val Phe Lys Gly Ala Pro Val Glu
        355                 360                 365

Leu Lys Cys Asn Tyr Ser Tyr Ser Gly Ser Pro Glu Leu Phe Trp Tyr
        370                 375                 380

Val Gln Tyr Ser Arg Gln Arg Leu Gln Leu Leu Leu Arg His Ile Ser
385                 390                 395                 400

Arg Glu Ser Ile Lys Gly Phe Thr Ala Asp Leu Asn Lys Gly Glu Thr
                405                 410                 415
```

-continued

```
Ser Phe His Leu Lys Lys Pro Phe Ala Gln Glu Glu Asp Ser Ala Met
        420             425             430

Tyr Tyr Cys Ala Leu Leu Gln Gly Ala Gln Lys Leu Val Phe Gly Gln
        435             440             445

Gly Thr Arg Leu Thr Ile Asn Pro Asn Ile Gln Asn Pro Glu Pro Ala
    450             455             460

Val Tyr Gln Leu Lys Asp Pro Arg Ser Gln Asp Ser Thr Leu Cys Leu
465             470             475             480

Phe Thr Asp Phe Asp Ser Gln Ile Asn Val Pro Lys Thr Met Glu Ser
            485             490             495

Gly Thr Phe Ile Thr Asp Lys Cys Val Leu Asp Met Lys Ala Met Asp
        500             505             510

Ser Lys Ser Asn Gly Ala Ile Ala Trp Ser Asn Gln Thr Ser Phe Thr
        515             520             525

Cys Gln Asp Ile Phe Lys Glu Thr Asn Ala Thr Tyr Pro Ser Ser Asp
        530             535             540

Val Pro Cys Asp Ala Thr Leu Thr Glu Lys Ser Phe Glu Thr Asp Met
545             550             555             560

Asn Leu Asn Phe Gln Asn Leu Leu Val Ile Val Leu Arg Ile Leu Leu
            565             570             575

Leu Lys Val Ala Gly Phe Asn Leu Leu Met Thr Leu Arg Leu Trp Ser
            580             585             590

Ser
```

<210> SEQ ID NO 38
<211> LENGTH: 1782
<212> TYPE: DNA
<213> ORGANISM: Artificial Sequence
<220> FEATURE:
<223> OTHER INFORMATION: Synthetic

<400> SEQUENCE: 38

```
atggcctccc tgctgctgct gctgctgggc ctgggaagcg tgttcagcgc cgtgatctct    60
cagaagccca gcagagatat ctgccagagg ggcaccagcc tgacaatcca gtgtcaggtg   120
gactcccagg tgaccatgat gttctggtac agacagcagc tggccagag cctgaccctg    180 atcgccacag ccaaccaggg ctctgaggcc acctatgaga gcggcttcgt gatcgataag   240
tttccaatct ccaggcccaa cctgacattc tctaccctga cagtgtccaa tatgtctccc   300
gaggatagct ccatctacct gtgcagcgtg agtccggcc aggactacgg ctataccttt    360
ggcagcggaa ccaggctgac agtggtggag acctgcgga acgtgacacc ccctaaggtg    420
agcctgttcg agccctccaa ggccgagatc gccaataagc agaaggccac cctggtgtgc   480
ctggccagag gcttctttcc tgatcacgtg agctgtctt ggtgggtgaa cggcaaggag    540
gtgcacagcg gcgtgtgcac cgacccacag gcctacaagg agtctaatta cagctattgt   600
ctgtctagcc ggctgagagt gtccgccaca ttttggcaca accctagaaa tcacttcagg   660
tgccaggtgc agtttcacgg cctgtctgag gaggataagt ggccagaggg cagcccaaag   720
ccagtgaccc agaacatctc cgccgaggca tggggaaggg cagactgtgg aatcacctct   780
gccagctatc agcagggcgt gctgagcgcc acaatcctgt acgagatcct gctgggcaag   840 gccacctgt atgccgtgct ggtgagcaca ctggtggtca tggctatggt gaagcggaag    900
aactcccggg ccaagagatc cggatctgga gccaccaatt tctctctgct gaagcaggcc   960
ggcgatgtgg aggagaatcc tggcccaatg aagcctacac tgatcagcgt gctggtcatc  1020
```

-continued

```
atcttcatcc tgaggggaac ccgcgcccag agggtgacac agcccgagaa gctgctgagc      1080
gtgtttaagg gcgcccctgt ggagctgaag tgcaactaca gctattccgg ctctccagag      1140
ctgttctggt acgtgcagta ttccaggcag cgcctgcagc tgctgctgag gcacatctcc      1200
cgggagtcta tcaagggctt taccgccgat ctgaataagg gcgagacaag cttccacctg      1260
aagaagccct ttgcccagga ggaggactcc gccatgtact attgtgcact gctgcaggga      1320
gcacagaagc tggtgttcgg acagggaacc aggctgacaa tcaacccaaa tatccagaac      1380
cccgagcctg ccgtgtacca gctgaaggac ccccggagcc aggattccac cctgtgcctg      1440
ttcacagact ttgattccca gatcaatgtg cccaagacaa tggagtctgg cacctttatc      1500
acagacaagt gcgtgctgga catgaaggct atggacagca agtccaacgg cgccatcgcc      1560
tggtccaatc agacctcttt cacatgccag gatatcttta aggagacaaa cgccacatat      1620
ccttcctctg acgtgccatg tgatgccacc ctgacagaga agagcttcga gacagacatg      1680
aacctgaatt ttcagaacct gctggtcatc gtgctgagaa tcctgctgct gaaggtggcc      1740
ggcttcaatc tgctgatgac actgaggctg tggagctcct ga                        1782
```

```
<210> SEQ ID NO 39
<211> LENGTH: 381
<212> TYPE: DNA
<213> ORGANISM: Homo sapiens

<400> SEQUENCE: 39
atgaagccta cactgatcag cgtgctggtc atcatcttca tcctgagggg aacccgcgcc        60
cagagggtga cacagcccga gaagctgctg agcgtgttta agggcgcccc tgtggagctg       120
aagtgcaact acagctattc cggctctcca gagctgttct ggtacgtgca gtattccagg       180
cagcgcctgc agctgctgct gaggcacatc tcccgggagt ctatcaaggg ctttaccgcc       240
gatctgaata agggcgagac aagcttccac ctgaagaagc cctttgccca ggaggaggac       300
tccgccatgt actattgtgc actgctgcag ggagcacaga agctggtgtt cggacaggga       360
accaggctga caatcaacccc a                                               381
```

```
<210> SEQ ID NO 40
<211> LENGTH: 387
<212> TYPE: DNA
<213> ORGANISM: Homo sapiens

<400> SEQUENCE: 40
atggcctccc tgctgctgct gctgctgggc ctgggaagcg tgttcagcgc cgtgatctct        60
cagaagccca gcagagatat ctgccagagg ggcaccagcc tgacaatcca gtgtcaggtg       120
gactcccagg tgaccatgat gttctggtac agacagcagc ctggccagag cctgaccctg       180
atcgccacag ccaaccaggg ctctgaggcc acctatgaga gcggcttcgt gatcgataag       240
tttccaatct ccaggcccaa cctgacattc tctaccctga cagtgtccaa tatgtctccc       300
gaggatagct ccatctacct gtgcagcgtg agtccggcc aggactacgg ctataccttt       360
ggcagcggaa ccaggctgac agtggtg                                          387
```

HLA CLASS II-RESTRICTED DRB T CELL RECEPTORS AGAINST RAS WITH G12V MUTATION

CROSS-REFERENCE TO RELATED APPLICATIONS

This patent application is the U.S. national stage of International Patent Application No. PCT/US2021/041737, filed Jul. 15, 2021, which claims the benefit of U.S. Provisional Patent Application No. 63/052,502, filed Jul. 16, 2020, each of which is incorporated by reference in its entirety herein.

STATEMENT REGARDING FEDERALLY SPONSORED RESEARCH OR DEVELOPMENT

This invention was made with Government support under project number ZIABC010984 by the National Institutes of Health, National Cancer Institute. The Government has certain rights in the invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 58,467 Byte ASCII (Text) file named "766537 ST25.txt." dated Jan. 11, 2023.

BACKGROUND OF THE INVENTION

Some cancers may have very limited treatment options, particularly when the cancer becomes metastatic and unresectable. Despite advances in treatments such as, for example, surgery, chemotherapy, and radiation therapy, the prognosis for many cancers, such as, for example, pancreatic, colorectal, lung, endometrial, ovarian, and prostate cancers, may be poor. Accordingly, there exists an unmet need for additional treatments for cancer.

BRIEF SUMMARY OF THE INVENTION

An embodiment of the invention provides an isolated or purified T-cell receptor (TCR) comprising the amino acid sequences of: (a) all of SEQ ID NOs: 1-3, (b) all of SEQ ID NOs: 4-6, or (c) all of SEQ ID NOs: 1-6, wherein the TCR has antigenic specificity for a mutated human RAS amino acid sequence with a substitution of glycine at position 12 with valine, wherein the mutated human RAS amino acid sequence is a mutated human Kirsten rat sarcoma viral oncogene homolog (KRAS), a mutated human Harvey rat sarcoma viral oncogene homolog (HRAS), or a mutated human Neuroblastoma rat sarcoma viral oncogene homolog (NRAS) amino acid sequence, and wherein position 12 is defined by reference to the wild-type human KRAS, wild-type human HRAS, or wild-type human NRAS protein, respectively.

Another embodiment of the invention provides an isolated or purified polypeptide comprising a functional portion of the inventive TCR, wherein the functional portion comprises the amino acid sequences of: (a) all of SEQ ID NOs: 1-3, (b) all of SEQ ID NOs: 4-6, or (c) all of SEQ ID NOs: 1-6.

Still another embodiment of the invention provides an isolated or purified protein comprising a first polypeptide chain comprising the amino acid sequences of SEQ ID NOs:

1-3 and a second polypeptide chain comprising the amino acid sequences of SEQ ID NOs: 4-6.

Embodiments of the invention further provide nucleic acids, recombinant expression vectors, host cells, populations of cells, and pharmaceutical compositions relating to the inventive TCRs, polypeptides, and proteins.

An embodiment of the invention provides an isolated or purified nucleic acid comprising, from 5' to 3', a first nucleic acid sequence and a second nucleotide sequence, wherein the first and second nucleotide sequence, respectively, encode the amino sequences of SEQ ID NOs: 7 and 8; 8 and 7; 9 and 10; or 10 and 9.

Methods of detecting the presence of cancer in a mammal, methods of treating or preventing cancer in a mammal, methods of inducing an immune response against a cancer in a mammal, methods of producing a host cell expressing a TCR that has antigenic specificity for the peptide of MTEYKLVVVGAVGVGKSALTIQLI (SEQ ID NO: 34), and methods of producing the inventive TCRs, polypeptides, and proteins, are further provided by embodiments of the invention.

BRIEF DESCRIPTION OF THE SEVERAL VIEWS OF THE DRAWING(S)

Figure 1B:
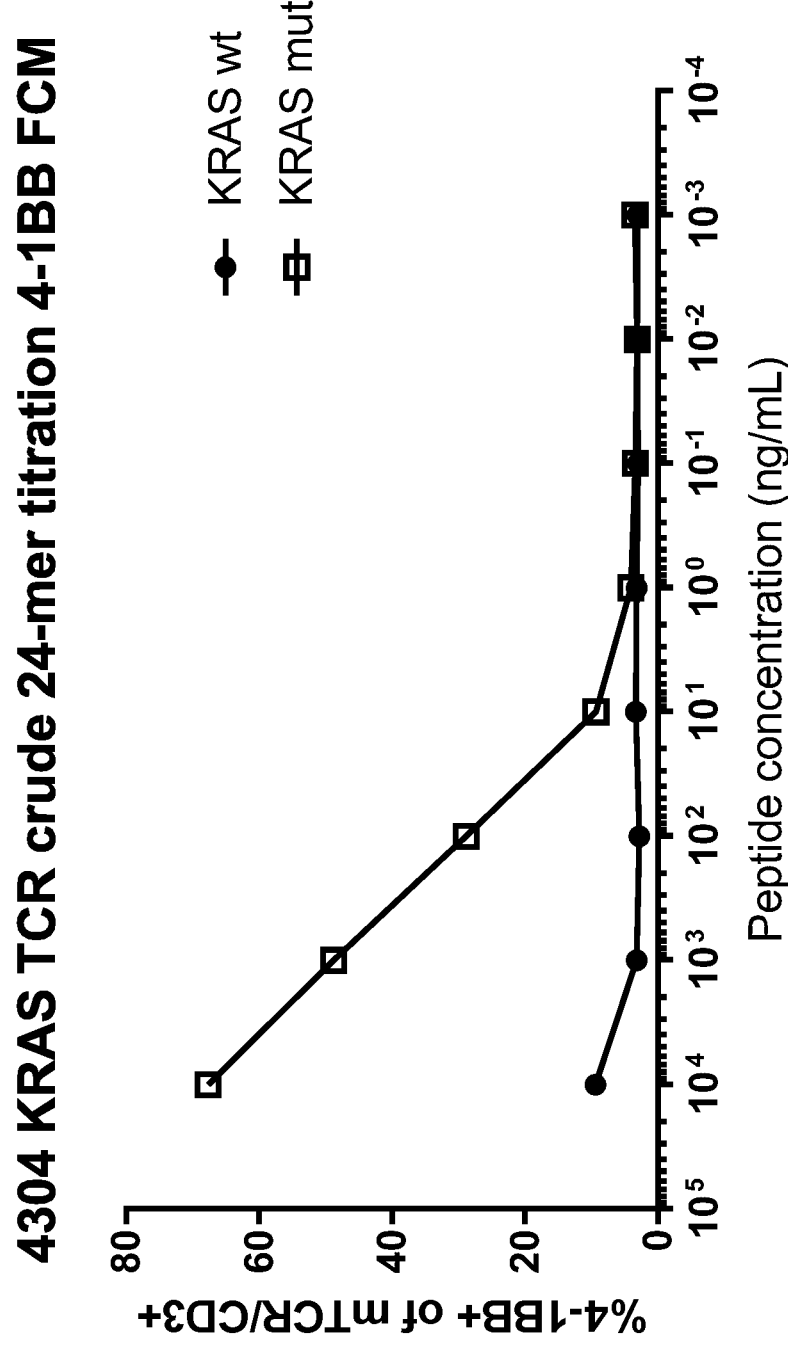

FIGS. 1A-1B are graphs showing the amount of IFN-γ secretion (pg/mL) (FIG. 1A) or the percentage of TCR murine constant region (mTCR) positive/CD$^{3+}$ cells which were positive for 4-1BB expression (FIG. 1B) following co-culture of target cells with effector cells. The effector cells were T cells transduced with the 4304 TCR1. Target cells were DCs pulsed with the indicated concentrations (ng/ml) of G12V 24-mer peptide (squares) (KRAS mut) or the corresponding WT 24-mer peptide (circles) (KRAS wt).

Figure 2:
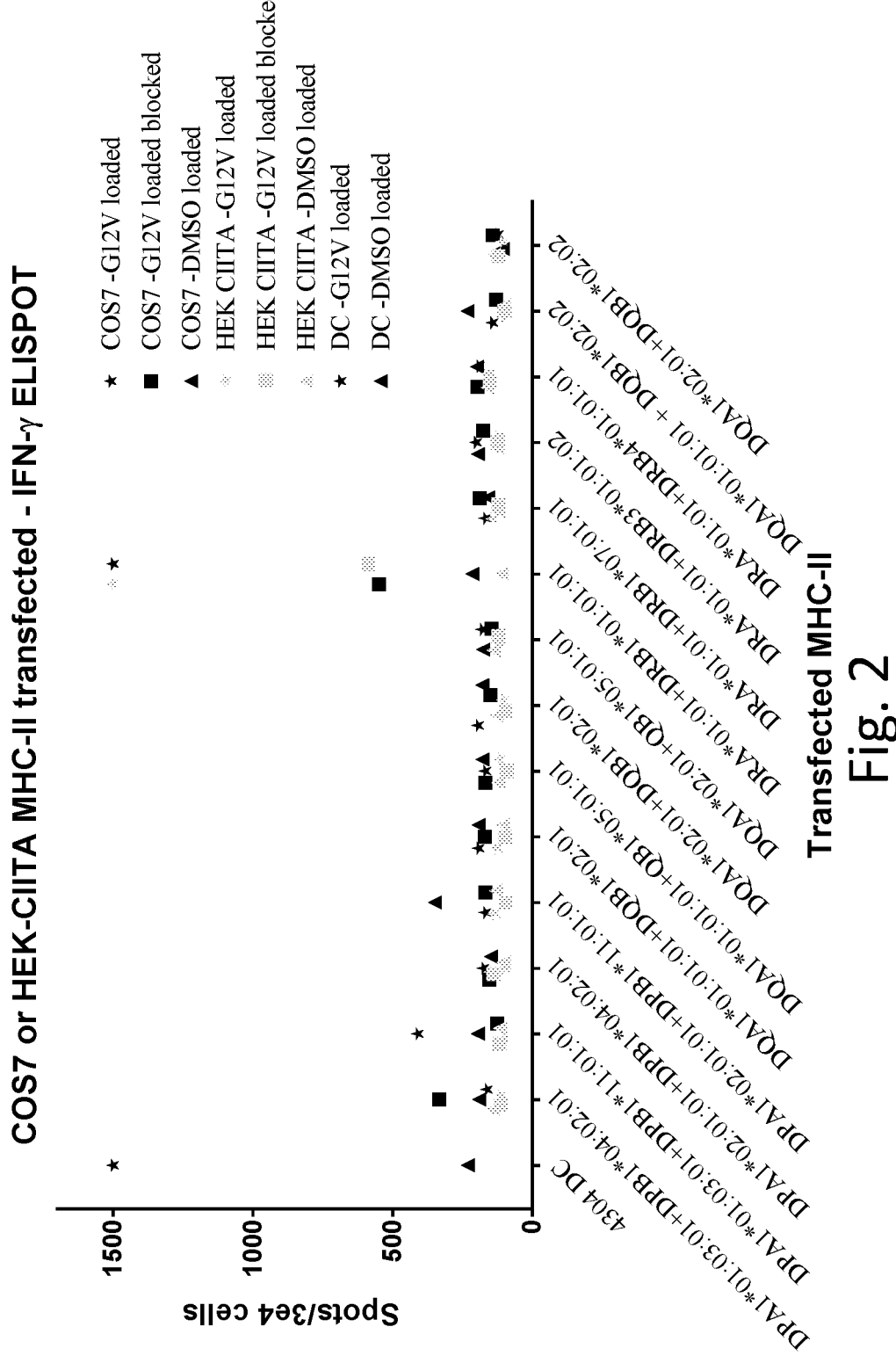

FIG. 2 is a graph showing IFN-γ secretion (spots/3e4 cells) measured by ELISPOT assay following co-culture of effector cells with target cells. Effector cells were healthy donor PBL transduced with the 4304 TCR1. Target cells were COST or HEK 293 cells independently transfected with one of the HLA Class II heterodimers shown. The target cells were loaded with the G12V 24-mer peptide and were cultured in the presence or absence of an antibody which blocked the respective HLA Class II molecule previously transfected. Target cells cultured with DMSO served as a negative control. Autologous DC from patent 4304 co-cultured with (i) the G12V 24-mer peptide served as a positive control and (ii) DMSO served as a negative control.

DETAILED DESCRIPTION OF THE INVENTION

RAS family proteins belong to the large family of small GTPases. Without being bound to a particular theory or mechanism, it is believed that, when mutated, RAS proteins may be involved in signal transduction early in the oncogenesis of many human cancers. A single amino acid substitution may activate the protein. The mutated RAS protein product may be constitutively activated. Mutated RAS proteins may be expressed in any of a variety of human cancers such as, for example, pancreatic (e.g., pancreatic carcinoma), colorectal, lung (e.g., lung adenocarcinoma), endometrial, ovarian (e.g., epithelial ovarian cancer), and prostate cancers. The human RAS family proteins include KRAS, HRAS, and NRAS.

KRAS is also referred to as GTPase KRas, V-Ki-Ras2 Kirsten rat sarcoma viral oncogene, or KRAS2. There are two transcript variants of KRAS: KRAS variant A and KRAS variant B. Wild-type (WT) KRAS variant A has the amino acid sequence of SEQ ID NO: 11. WT KRAS variant B has the amino acid sequence of SEQ ID NO: 12. Hereinafter, references to "KRAS" (mutated or unmutated (WT)) refer to both variant A and variant B, unless specified otherwise. When activated, mutated KRAS binds to guanosine-5'-triphosphate (GTP) and converts GTP to guanosine 5'-diphosphate (GDP).

HRAS is another member of the RAS protein family. HRAS is also referred to as Harvey Rat Sarcoma Viral Oncoprotein, V-Ha-Ras Harvey Rat Sarcoma Viral Oncogene Homolog, or Ras Family Small GTP Binding Protein H-Ras. WT HRAS has the amino acid sequence of SEQ ID NO: 13.

NRAS is still another member of the RAS protein family. NRAS is also referred to as GTPase NRas, V-Ras Neuroblastoma RAS Viral Oncogene Homolog, or NRAS1. WT NRAS has the amino acid sequence of SEQ ID NO: 14.

An embodiment of the invention provides an isolated or purified TCR, wherein the TCR has antigenic specificity for a mutated human RAS amino acid sequence with a substitution of glycine at position 12 with valine, wherein the mutated human RAS amino acid sequence is a mutated human KRAS, a mutated human HRAS, or a mutated human NRAS amino acid sequence, and wherein position 12 is defined by reference to the WT human KRAS, WT human HRAS, or WT human NRAS protein, respectively. Hereinafter, references to a "TCR" also refer to functional portions and functional variants of the TCR, unless specified otherwise.

The mutated human RAS amino acid sequence may be a mutated human KRAS amino acid sequence, a mutated human HRAS amino acid sequence, or a mutated human NRAS amino acid sequence. The amino acid sequences of WT human KRAS, NRAS, and HRAS protein each have a length of 188 or 189 amino acid residues and have a high degree of identity to one another. For example, the amino acid sequence of the WT human NRAS protein is 86.8% identical to that of the WT human KRAS protein. Amino acid residues 1-86 of the WT human NRAS protein and the WT human KRAS protein are 100% identical. The amino acid sequence of the WT human HRAS protein is 86.3% identical to that of the WT human KRAS protein. Amino acid residues 1-94 of the WT human HRAS protein and the WT human KRAS protein are 100% identical. Hereinafter, references to "RAS" (mutated or unmutated (WT)) collectively refer to KRAS, HRAS, and NRAS, unless specified otherwise.

In an embodiment of the invention, the mutated human RAS amino acid sequence comprises a human RAS amino acid sequence with a substitution of glycine at position 12 with valine, wherein position 12 is defined by reference to the corresponding WT RAS protein. The WT RAS protein may be any one of WT KRAS protein (SEQ ID NO: 11 or 12), WT HRAS protein (SEQ ID NO: 13), or WT NRAS protein (SEQ ID NO: 14) because, as explained above, amino acid residues 1-86 of the WT human NRAS protein and the WT human KRAS protein are 100% identical, and amino acid residues 1-94 of the WT human HRAS protein and the WT human KRAS protein are 100% identical. Accordingly, the amino acid residue at position 12 of each of WT KRAS, WT HRAS, and WT NRAS protein is the same, namely, glycine.

The mutated human RAS amino acid sequence has a substitution of glycine at position 12 with valine. In this regard, embodiments of the invention provide TCRs with antigenic specificity for any human RAS protein, polypeptide or peptide amino acid sequence with a G12V mutation.

Mutations and substitutions of RAS are defined herein by reference to the amino acid sequence of the corresponding WT RAS protein. Thus, mutations and substitutions of RAS are described herein by reference to the amino acid residue present at a particular position in WT RAS protein (namely, position 12), followed by the position number, followed by the amino acid residue with which that residue has been replaced in the particular mutation or substitution under discussion. A RAS amino acid sequence (e.g., a RAS peptide) may comprise fewer than all of the amino acid residues of the full-length, WT RAS protein. Accordingly, position 12 is defined herein by reference to the WT full-length RAS protein (namely, any one of SEQ ID NOs: 11-14) with the understanding that the actual position of the corresponding residue in a particular example of a RAS amino acid sequence may be different. When the positions are as defined by any one of SEQ ID NOs: 11-14, the term "G12" refers to the glycine normally present at position 12 of any one of SEQ ID NOs: 11-14, and "G12V" indicates that the glycine normally present at position 12 of any one of SEQ ID NOs: 11-14 is replaced by valine. For example, when a particular example of a RAS amino acid sequence is, e.g., TEYKLVVVGAGGVGKSALTIQLI (SEQ ID NO: 36) (an exemplary WT KRAS peptide corresponding to contiguous amino acid residues 2 to 24 of SEQ ID NO: 11), "G12V" refers to a substitution of the underlined glycine in SEQ ID NO: 36 with valine, even though the actual position of the underlined glycine in SEQ ID NO: 36 is 11. Human RAS amino acid sequences with the G12V mutation are hereinafter referred to as "G12V RAS" or "G12V".

Examples of full-length RAS proteins with the G12V mutation are set forth in Table 1 below.

TABLE 1

| Mutated Full-Length RAS Protein | SEQ ID NO: |
|---|---|
| G12V KRAS variant A | 15 |
| G12V KRAS variant B | 16 |
| G12V HRAS | 17 |
| G12V NRAS | 18 |

In an embodiment of the invention, the TCR has antigenic specificity for a RAS peptide with the G12V mutation described above, wherein the G12V RAS peptide has any length. In an embodiment of the invention, the G12V RAS peptide has any length suitable for binding to any of the HLA Class II molecules described herein. For example, the TCR may have antigenic specificity for a RAS peptide with the G12V mutation, the RAS peptide having a length of about 11 to about 30 amino acid residues, about 12 to about 24 amino acid residues, or about 18 to about 20 amino acid residues. The G12V RAS peptide may comprise any contiguous amino acid residues of mutated RAS protein which include the G12V mutation. In an embodiment of the invention, the TCR may have antigenic specificity for a RAS peptide with the G12V mutation, the mutated RAS peptide having a length of about 30 amino acid residues, about 29 amino acid residues, about 28 amino acid residues, about 27 amino acid residues, about 26 amino acid residues, about 25 amino acid residues, about 24 amino acid residues, about 23 amino acid residues, about 22 amino acid residues, about 21 amino acid residues, about 20 amino acid residues, about 19 amino acid residues, about 18 amino acid residues, about 17 amino acid residues, about 16 amino acid residues, about 15 amino acid residues, about 14 amino acid residues, about 13 amino acid residues, about 12 amino acid residues, about 11 amino acid residues, or a range of any two of the foregoing values. An example of a specific peptide with the G12V mutation, which may be recognized by the inventive TCRs, is MTEYKLVVVGAVGVGKSALTIQLI (SEQ ID NO: 34). In an embodiment of the invention, the TCR has antigenic specificity for the mutated human RAS amino acid sequence of SEQ ID NO: 34. In an embodiment of the invention, the TCR does not have antigenic specificity for the wild-type human RAS amino acid sequence of MTEYKLVVVGAGGVGKSALTIQLI (SEQ ID NO: 35).

In an embodiment of the invention, the inventive TCRs are able to recognize G12V RAS presented by an HLA Class II molecule. In this regard, the TCR may elicit an immune response upon binding to G12V RAS within the context of an HLA Class II molecule. The inventive TCRs are able to recognize G12V RAS that is presented by an HLA Class II molecule and may bind to the HLA Class II molecule in addition to G12V RAS.

In an embodiment of the invention, the HLA Class II molecule is an HLA-DR heterodimer. The HLA-DR heterodimer is a cell surface receptor including an α chain and a β chain. The HLA-DR α chain is encoded by the HLA-DRA gene. The HLA-DR β chain is encoded by the HLA-DRB1 gene, the HLA-DRB3 gene, HLA-DRB4 gene, or the HLA-DRB5 gene. Examples of molecules encoded by the HLA-DRB1 gene may include, but are not limited to, HLA-DR1, HLA-DR2, HLA-DR3, HLA-DR4, HLA-DR5, HLA-DR6, HLA-DR7, HLA-DR8, HLA-DR9, HLA-DR10, HLA-DR11, HLA-DR12, HLA-DR13, HLA-DR14, HLA-DR15, HLA-DR16, and HLA-DR17. The HLA-DRB3 gene encodes HLA-DR52. The HLA-DRB4 gene encodes HLA-DR53. The HLA-DRB5 gene encodes HLA-DR51. In an embodiment of the invention, the HLA Class II molecule comprises a HLA-DR α chain in combination with a HLA-DR β chain encoded by the HLA-DRB1 gene. In an especially preferred embodiment, the HLA Class II molecule is an HLA-DRB1*01:HLA-DRA*01 heterodimer (namely, expressed by the HLA-DRB1*01:HLA-DRA*01 alleles). In an embodiment, the HLA-DR β chain is encoded by the HLA-DRB1*01:01 allele.

The TCRs of the invention may provide any one or more of a variety of advantages, including when expressed by cells used for adoptive cell transfer. G12V RAS is expressed by cancer cells and is not expressed by normal, noncancerous cells. Without being bound to a particular theory or mechanism, it is believed that the inventive TCRs advantageously target the destruction of cancer cells while minimizing or eliminating the destruction of normal, non-cancerous cells, thereby reducing, for example, by minimizing or eliminating, toxicity. Moreover, because the G12V mutation is likely to occur in the early stages of tumorigenesis, the G12V RAS mutation may be expressed on substantially all of a patient's cancer cells. The inventive TCRs may, advantageously, successfully treat or prevent G12V RAS-positive cancers that do not respond to other types of treatment such as, for example, chemotherapy, surgery, or radiation. Additionally, the inventive TCRs may provide highly avid recognition of G12V RAS, which may provide the ability to recognize unmanipulated tumor cells (e.g., tumor cells that have not been treated with interferon (IFN)-γ, transfected with a vector encoding one or both of G12V RAS and the HLA-DRB1*01:HLA-DRA*01 heterodimer, pulsed with a G12V RAS peptide, or a combination thereof). KRAS mutations are found in about 70% of pancreatic cancer, 36% of colorectal cancer and 20% of lung cancer. Most commonly, mutations occur in the codon 12

(encoding glycine, G). The G12V RAS mutation is found in about 27% and about 8% of patients with pancreatic and colorectal cancers, respectively. Moreover, the HLA-DRB1*01 allele is commonly expressed by humans with Caucasian ethnicity. For example this allele is expressed by about 20% of humans with Caucasian ethnicity in the United States. If this allele is expressed by about 20% of humans with Caucasian ethnicity in the United States, and mutated RAS is expressed by about 30% of all cancer patients, and among RAS mutations, about 25% are G12V RAS, then the TCR has the potential to treat about 1.5% (0.2×0.3× 0.25=0.015) of all humans with Caucasian ethnicity with cancer in the U.S. Accordingly, the inventive TCRs may increase the number of immunotherapy-eligible cancer patients to include those patients that express the HLA-DRB1*01 allele who may not be eligible for immunotherapy using TCRs that recognize RAS presented by other MHC molecules. Moreover, the inventive TCRs, polypeptides and proteins comprise human CDR and variable region amino acid sequences, which may reduce the risk of rejection by the human immune system as compared to, e.g., TCRs, polypeptides and proteins comprising mouse CDR and variable region amino acid sequences.

The phrase "antigenic specificity," as used herein, means that the TCR can specifically bind to and immunologically recognize G12V RAS with high avidity. For example, a TCR may be considered to have "antigenic specificity" for G12V RAS if about $1 \times 10^4$ to about $1 \times 10^5$ T cells expressing the TCR secrete at least about 200 pg/mL or more (e.g., 200 pg/mL or more, 300 pg/mL or more, 400 pg/mL or more, 500 pg/mL or more, 600 pg/mL or more, 700 pg/mL or more, 1000 pg/mL or more, 5,000 pg/mL or more, 7,000 pg/mL or more, 10,000 pg/mL or more, 20,000 pg/mL or more, or a range defined by any two of the foregoing values) of IFN-γ upon co-culture with (a) antigen-negative, HLA Class II molecule positive target cells pulsed with a low concentration of G12V RAS peptide (e.g., about 0.05 ng/mL to about 10 ng/mL, 1 ng/mL, 2 ng/mL, 5 ng/mL, 8 ng/mL, 10 ng/mL, or a range defined by any two of the foregoing values) or (b) antigen-negative, HLA Class II molecule positive target cells into which a nucleotide sequence encoding G12V RAS has been introduced such that the target cell expresses G12V RAS. Cells expressing the inventive TCRs may also secrete IFN-γ upon co-culture with antigen-negative, HLA Class II molecule positive target cells pulsed with higher concentrations of G12V RAS peptide. The HLA Class II molecule may be any of the HLA Class II molecules described herein.

Alternatively or additionally, a TCR may be considered to have "antigenic specificity" for G12V RAS if T cells expressing the TCR secrete at least twice (e.g., five times) as much IFN-γ upon co-culture with (a) antigen-negative, HLA Class II molecule positive target cells pulsed with a low concentration of G12V RAS peptide or (b) antigen-negative, HLA Class II molecule positive target cells into which a nucleotide sequence encoding G12V RAS has been introduced such that the target cell expresses G12V RAS as compared to the amount of IFN-γ expressed by a negative control. The negative control may be, for example, (i) T cells expressing the TCR, co-cultured with (a) antigen-negative, HLA Class II molecule positive target cells pulsed with the same concentration of an irrelevant peptide (e.g., some other peptide with a different sequence from the G12V RAS peptide) or (b) antigen-negative, HLA Class II molecule positive target cells into which a nucleotide sequence encoding an irrelevant peptide has been introduced such that the target cell expresses the irrelevant peptide, or (ii) untransduced T cells (e.g., derived from PBMC, which do not express the TCR) co-cultured with (a) antigen-negative, HLA Class II molecule positive target cells pulsed with the same concentration of G12V RAS peptide or (b) antigen-negative, HLA Class II molecule positive target cells into which a nucleotide sequence encoding G12V RAS has been introduced such that the target cell expresses G12V RAS. The HLA Class II molecule expressed by the target cells of the negative control would be the same HLA Class II molecule expressed by the target cells that are co-cultured with the T cells being tested. The HLA Class II molecule may be any of the HLA Class II molecules described herein. IFN-γ secretion may be measured by methods known in the art such as, for example, enzyme-linked immunosorbent assay (ELISA).

Alternatively or additionally, a TCR may be considered to have "antigenic specificity" for G12V RAS if at least twice (e.g., five times) as many of the numbers of T cells expressing the TCR secrete IFN-γ upon co-culture with (a) antigen-negative, HLA Class II molecule positive target cells pulsed with a low concentration of G12V RAS peptide or (b) antigen-negative, HLA Class II molecule positive target cells into which a nucleotide sequence encoding G12V RAS has been introduced such that the target cell expresses G12V RAS as compared to the numbers of negative control T cells that secrete IFN-γ. The HLA Class II molecule, concentration of peptide, and the negative control may be as described herein with respect to other aspects of the invention. The numbers of cells secreting IFN-γ may be measured by methods known in the art such as, for example, ELISPOT.

Alternatively or additionally, a TCR may be considered to have "antigenic specificity" for G12V RAS if T cells expressing the TCR upregulate expression of one or more T-cell activation markers as measured by, for example, flow cytometry after stimulation with target cells expressing G12V RAS. Examples of T-cell activation markers include 4-1BB, OX40, CD107a, CD69, and cytokines that are upregulated upon antigen stimulation (e.g., tumor necrosis factor (TNF), interleukin (IL)-2, etc.).

An embodiment of the invention provides a TCR comprising two polypeptides (i.e., polypeptide chains), such as an alpha (α) chain of a TCR, a beta (β) chain of a TCR, a gamma (γ) chain of a TCR, a delta (δ) chain of a TCR, or a combination thereof. The polypeptides of the inventive TCR can comprise any amino acid sequence, provided that the TCR has antigenic specificity for G12V RAS. In some embodiments, the TCR is non-naturally occurring.

In an embodiment of the invention, the TCR comprises two polypeptide chains, each of which comprises a variable region comprising a complementarity determining region (CDR)1, a CDR2, and a CDR3 of a TCR. In an embodiment of the invention, the TCR comprises a first polypeptide chain comprising a CDR1 comprising the amino acid sequence of SEQ ID NO: 1 (CDR1 of a chain of 4304 TCR1), a CDR2 comprising the amino acid sequence of SEQ ID NO: 2 (CDR2 of a chain of 4304 TCR1), and a CDR3 comprising the amino acid sequence of SEQ ID NO: 3 (CDR3 of α chain of 4304 TCR1), and a second polypeptide chain comprising a CDR1 comprising the amino acid sequence of SEQ ID NO: 4 (CDR1 of β chain of 4304 TCR1), a CDR2 comprising the amino acid sequence of SEQ ID NO: 5 (CDR2 of β chain of 4304 TCR1), and a CDR3 comprising the amino acid sequence of SEQ ID NO: 6 (CDR3 of β chain of 4304 TCR1). In this regard, the inventive TCR can comprise any one or more of the amino acid sequences selected from the group consisting of SEQ ID NOs: 1-6. In an embodiment of the invention, the TCR comprises the amino acid sequences of: (a) all of SEQ ID NOs: 1-3, (b) all of SEQ ID NOs: 4-6, or (c) all of SEQ ID NOs: 1-6. In an especially preferred embodiment, the TCR comprises the amino acid sequences of all of SEQ ID NOs: 1-6.

In an embodiment of the invention, the TCR comprises an amino acid sequence of a variable region of a TCR comprising the CDRs set forth above. In this regard, the TCR can comprise the amino acid sequence of: (i) SEQ ID NO: 7 (predicted sequence of variable region of a chain of 4304 TCR1 without N-terminal signal peptide); (ii) SEQ ID NO: 8 (predicted sequence of variable region of β chain of 4304 TCR1 without N-terminal signal peptide); (iii) SEQ ID NO: 9 (variable region of α chain of 4304 TCR1 with N-terminal signal peptide); (iv) SEQ ID NO: 10 (variable region of β chain of 4304 TCR1 with N-terminal signal peptide); (v) both of SEQ ID NOs: 7 and 8; or (vi) both of SEQ ID NOs: 9 and 10. Preferably, the TCR comprises the amino acid sequences of (i) both of SEQ ID NOs: 7 and 8 or (ii) both of SEQ ID NOs: 9 and 10.

The inventive TCRs may further comprise an α chain constant region and a β chain constant region. The constant region may be derived from any suitable species such as, e.g., human or mouse. In an embodiment of the invention, the TCRs further comprise murine α and β chain constant regions or human α and β chain constant regions. As used herein, the term "murine" or "human," when referring to a TCR or any component of a TCR described herein (e.g., CDR, variable region, constant region, α chain, and/or β chain), means a TCR (or component thereof) which is derived from a mouse or a human, respectively, i.e., a TCR (or component thereof) that originated from or was, at one time, expressed by a mouse T cell or a human T cell, respectively.

An embodiment of the invention provides a chimeric TCR comprising a human variable region and a murine constant region, wherein the TCR has antigenic specificity for a mutated human RAS amino acid sequence with a substitution of glycine at position 12 with valine. The murine constant region may provide any one or more advantages. For example, the murine constant region may diminish mispairing of the inventive TCR with the endogenous TCRs of the host cell into which the inventive TCR is introduced. Alternatively or additionally, the murine constant region may increase expression of the inventive TCR as compared to the same TCR with a human constant region. The chimeric TCR may comprise the amino acid sequence of SEQ ID NO: 23 (WT murine α chain constant region), SEQ ID NO: 24 (WT murine β chain constant region), or both SEQ ID NOs: 23 and 24. Preferably, the inventive TCR comprises the amino acid sequences of both of SEQ ID NOs: 23 and 24. The chimeric TCR may comprise any of the murine constant regions described herein in combination with any of the CDR regions as described herein with respect to other aspects of the invention. In this regard, the TCR may comprise the amino acid sequences of: (a) all of SEQ ID NOs: 1-3 and 23, (b) all of SEQ ID NOs: 4-6 and 24, or (c) all of SEQ ID NOs: 1-6 and 23-24. In another embodiment of the invention, the chimeric TCR may comprise any of the murine constant regions described herein in combination with any of the variable regions described herein with respect to other aspects of the invention. In this regard, the TCR may comprise the amino acid sequences of: (i) both of SEQ ID NOs: 7 and 23, (ii) both of SEQ ID NOs: 8 and 24, (iii) both of SEQ ID NOs: 9 and 23, (iv) both of SEQ ID NOs: 10 and 24, (v) all of SEQ ID NOs: 7-8 and 23-24, or (vi) all of SEQ ID NOs: 9-10 and 23-24.

In an embodiment of the invention, the TCR comprises a substituted constant region. In this regard, the TCR may comprise the amino acid sequence of any of the TCRs described herein with one, two, three, or four amino acid substitution(s) in the constant region of one or both of the α and β chain. Preferably, the TCR comprises a murine constant region with one, two, three, or four amino acid substitution(s) in the murine constant region of one or both of the α and β chains. In an especially preferred embodiment, the TCR comprises a murine constant region with one, two, three, or four amino acid substitution(s) in the murine constant region of the α chain and one amino acid substitution in the murine constant region of the β chain. In some embodiments, the TCRs comprising the substituted constant region advantageously provide one or more of increased recognition of G12V RAS$^+$ targets, increased expression by a host cell, diminished mispairing with endogenous TCRs, and increased anti-tumor activity as compared to the parent TCR comprising an unsubstituted (wild-type) constant region. In general, the substituted amino acid sequences of the murine constant regions of the TCR α and β chains, SEQ ID NOs: 19 and 20, respectively, correspond with all or portions of the unsubstituted murine constant region amino acid sequences SEQ ID NOs: 23 and 24, respectively, with SEQ ID NO: 19 having one, two, three, or four amino acid substitution(s) when compared to SEQ ID NO: 23 and SEQ ID NO: 20 having one amino acid substitution when compared to SEQ ID NO: 24. In this regard, an embodiment of the invention provides a TCR comprising the amino acid sequences of (a) SEQ ID NO: 19 (constant region of a chain), wherein (i) X at position 48 is Thr or Cys; (ii) X at position 112 is Ser, Ala, Val, Leu, Ile, Pro, Phe, Met, or Trp; (iii) X at position 114 is Met, Ala, Val, Leu, Ile, Pro, Phe, or Trp; and (iv) X at position 115 is Gly, Ala, Val, Leu, Ile, Pro, Phe, Met, or Trp; (b) SEQ ID NO: 20 (constant region of β chain), wherein X at position 57 is Ser or Cys; or (c) both of SEQ ID NOs: 19 and 20. In an embodiment of the invention, the TCR comprising SEQ ID NO: 19 does not comprise SEQ ID NO: 23 (unsubstituted murine constant region of a chain). In an embodiment of the invention, the TCR comprising SEQ ID NO: 20 does not comprise SEQ ID NO: 24 (unsubstituted murine constant region of β chain).

In an embodiment of the invention, the TCR comprises an α chain comprising a variable region and a constant region and a β chain comprising a variable region and a constant region. In this regard, the TCR may comprise (a) an α chain comprising the amino acid sequence of SEQ ID NO: 25 (α chain of 4304 TCR1 with N-terminal signal peptide), wherein: (i) X at position 175 of SEQ ID NO: 25 is Thr or Cys; (ii) X at position 239 of SEQ ID NO: 25 is Ser, Ala, Val, Leu, Ile, Pro, Phe, Met, or Trp; (iii) X at position 241 of SEQ ID NO: 25 is Met, Ala, Val, Leu, Ile, Pro, Phe, or Trp; and (iv) X at position 242 of SEQ ID NO: 25 is Gly, Ala, Val, Leu, Ile, Pro, Phe, Met, or Trp; (b) a β chain comprising the amino acid sequence of SEQ ID NO: 26 (β chain of 4304 TCR1 with N-terminal signal peptide), wherein X at position 186 of SEQ ID NO: 26 is Ser or Cys; (c) both of SEQ ID NOs: 25 and 26; (d) an α chain comprising the amino acid sequence of SEQ ID NO: 27 (predicted sequence of a chain of 4304 TCR1 without N-terminal signal peptide), wherein: (i) X at position 156 of SEQ ID NO: 27 is Thr or Cys; (ii) X at position 220 of SEQ ID NO: 27 is Ser, Ala, Val, Leu, Ile, Pro, Phe, Met, or Trp; (iii) X at position 222 of SEQ ID NO: 27 is Met, Ala, Val, Leu, Ile, Pro, Phe, or Trp; and (iv) X at position 223 of SEQ ID NO: 27 is Gly, Ala, Val, Leu, Ile, Pro, Phe, Met, or Trp; (e) a β chain comprising the amino acid sequence of SEQ ID NO: 28 (predicted sequence of β chain of 4304 TCR1 without N-terminal signal peptide), wherein X at position 171 of SEQ ID NO: 28 is Ser or Cys;

(f) both of SEQ ID NOs: 27 and 28; (g) SEQ ID NO: 29 (a chain of cysteine-substituted, LVL-modified 4304 TCR1 with N-terminal signal sequence); (h) SEQ ID NO: 30 (β chain of cysteine-substituted, LVL-modified 4304 TCR1 with N-terminal signal sequence); (i) SEQ ID NO: 31 (predicted sequence of a chain of cysteine-substituted, LVL-modified 4304 TCR1 without N-terminal signal sequence); or (j) SEQ ID NO: 32 (predicted sequence of β chain of cysteine-substituted, LVL-modified 4304 TCR1 without N-terminal signal sequence).

In an embodiment of the invention, the substituted constant region includes cysteine substitutions in the constant region of one or both of the α and β chains to provide a cysteine-substituted TCR. Opposing cysteines in the α and the β chains provide a disulfide bond that links the constant regions of the α and the β chains of the substituted TCR to one another and which is not present in a TCR comprising the unsubstituted murine constant regions. In this regard, the TCR may be a cysteine-substituted TCR in which one or both of the native Thr at position 48 (Thr48) of SEQ ID NO: 23 and the native Ser at position 57 (Ser57) of SEQ ID NO: 24 may be substituted with Cys. Preferably, both of the native Thr48 of SEQ ID NO: 23 and the native Ser57 of SEQ ID NO: 24 are substituted with Cys. Examples of cysteine-substituted TCR constant regions sequences are set forth in Table 2. In an embodiment of the invention, the cysteine-substituted TCR comprises (i) SEQ ID NO: 19, (ii) SEQ ID NO: 20, or (iii) both of SEQ ID NOs: 19 and 20, wherein both of SEQ ID NOs: 19 and 20 are as defined in Table 2. The cysteine-substituted TCRs of the invention may include the substituted constant region in addition to any of the CDRs or variable regions described herein.

In an embodiment of the invention, the cysteine-substituted, chimeric TCR comprises a full length α chain and a full-length β chain. Examples of cysteine-substituted, chimeric TCR α chain and β chain sequences are set forth in Table 2. In an embodiment of the invention, the TCR comprises: (i) SEQ ID NO: 25, (ii) SEQ ID NO: 26, (iii) SEQ ID NO: 27, (iv) SEQ ID NO: 28, (v) both of SEQ ID NOs: 25 and 26, or (vi) both of SEQ ID NOs: 27 and 28, wherein all of SEQ ID NOs: 25-28 are as defined in Table 2.

TABLE 2

| SEQ ID NO: | Definitions of "X" |
|---|---|
| SEQ ID NO: 19 (constant region α chain) | X at position 48 is Cys, X at position 112 is Ser, X at position 114 is Met, and X at position 115 is Gly. |
| SEQ ID NO: 20 (constant region β chain) | X at position 57 is Cys |
| SEQ ID NO: 25 (4304 TCR1 α chain with N-terminal signal peptide) | X at position 175 is Cys, X at position 239 is Ser, X at position 241 is Met, and X at position 242 is Gly. |
| SEQ ID NO: 26 (4304 TCR1 β chain with N-terminal signal peptide) | X at position 186 is Cys |
| SEQ ID NO: 27 (4304 TCR1 α chain predicted sequence without N-terminal signal peptide) | X at position 156 is Cys, X at position 220 is Ser, X at position 222 is Met, and X at position 223 is Gly. |
| SEQ ID NO: 28 (4304 TCR1 β chain predicted sequence without N-terminal signal peptide) | X at position 171 is Cys |

In an embodiment of the invention, the substituted amino acid sequence includes substitutions of one, two, or three amino acids in the transmembrane (TM) domain of the constant region of the α chain with a hydrophobic amino acid to provide a hydrophobic amino acid-substituted TCR (also referred to herein as an "LVL-modified TCR"). The hydrophobic amino acid substitution(s) in the TM domain of the TCR may increase the hydrophobicity of the TM domain of the TCR as compared to a TCR that lacks the hydrophobic amino acid substitution(s) in the TM domain. In this regard, the TCR is an LVL-modified TCR in which one, two, or three of the native Ser112, Met114, and Gly115 of SEQ ID NO: 23 may, independently, be substituted with Ala, Val, Leu, Ile, Pro, Phe, Met, or Trp; preferably with Leu, Ile, or Val. Preferably, all three of the native Ser112, Met114, and Gly115 of SEQ ID NO: 23 may, independently, be substituted with Ala, Val, Leu, Ile, Pro, Phe, Met, or Trp; preferably with Leu, Ile, or Val. In an embodiment of the invention, the LVL-modified TCR comprises (i) SEQ ID NO: 19, (ii) SEQ ID NO: 20, or (iii) both of SEQ ID NOs: 19 and 20, wherein both of SEQ ID NOs: 19 and 20 are as defined in Table 3. The LVL-modified TCRs of the invention may include the substituted constant region in addition to any of the CDRs or variable regions described herein.

In an embodiment of the invention, the LVL-modified TCR comprises a full length α chain and a full-length β chain. Examples of LVL-modified TCR α chain and β chain sequences are set forth in Table 3. In an embodiment of the invention, the TCR comprises: (i) SEQ ID NO: 25, (ii) SEQ ID NO: 26, (iii) SEQ ID NO: 27, (iv) SEQ ID NO: 28, (v) both of SEQ ID NOs: 25 and 26, or (vi) both of SEQ ID NOs: 27 and 28, wherein all of SEQ ID NOs: 25-28 are as defined in Table 3.

TABLE 3

| SEQ ID NO: | Definitions of "X" |
|---|---|
| SEQ ID NO: 19 (constant region α chain) | X at position 48 is Thr; X at position 112 is Ser, Ala, Val, Leu, Ile, Pro, Phe, Met, or Trp; preferably wherein X at position 112 is Leu, Ile, or Val; especially preferably wherein X at position 112 is Leu; X at position 114 is Met, Ala, Val, Leu, Ile, Pro, Phe, or Trp; preferably wherein X at position 114 is Leu, Ile, or Val; especially preferably wherein X at position 114 is Ile; and X at position 115 is Gly, Ala, Val, Leu, Ile, Pro, Phe, Met, or Trp; preferably wherein X at position 115 is Leu, Ile, or Val; especially preferably wherein X at position 115 is Val; wherein SEQ ID NO: 19 does not comprise SEQ ID NO: 23 (unsubstituted α chain constant region) |
| SEQ ID NO: 20 (constant region β chain) | X at position 57 is Ser |
| SEQ ID NO: 25 (4304 TCR1 α chain) (with N-terminal signal peptide) | X at position 175 is Thr; X at position 239 is Ser, Ala, Val, Leu, Ile, Pro, Phe, Met, or Trp; preferably wherein X at position 239 is Leu, Ile, or Val; especially preferably wherein X at position 239 is Leu; X at position 241 is Met, Ala, Val, Leu, Ile, Pro, Phe, or Trp; preferably wherein X at position 241 is Leu, Ile, or Val; especially preferably wherein X at position 241 is Ile; and X at position 242 is Gly, Ala, Val, Leu, Ile, Pro, Phe, Met, or Trp; preferably wherein X at position 242 is Leu, Ile, or Val; especially preferably wherein X at position 242 is Val, wherein SEQ ID NO: 25 does not comprise SEQ ID NO: 23 (unsubstituted α chain constant region) |
| SEQ ID NO: 26 (4304 TCR1 β chain) (with N-terminal signal peptide) | X at position 186 is Ser |
| SEQ ID NO: 27 (4304 TCR1 α chain) (predicted sequence without N-terminal signal peptide) | X at position 156 is Thr; X at position 220 is Ser, Ala, Val, Leu, Ile, Pro, Phe, Met, or Trp; preferably wherein X at position 220 is Leu, Ile, or Val; especially preferably wherein X at position 220 is Leu; X at position 222 is Met, Ala, Val, Leu, Ile, Pro, Phe, or Trp; preferably wherein X at position 222 is Leu, Ile, or Val; especially preferably wherein X at position 222 is Ile; and X at position 223 is Gly, Ala, Val, Leu, Ile, Pro, Phe, Met, or Trp; preferably wherein X at position 223 is Leu, Ile, or Val; especially preferably wherein X at position 223 is Val, wherein SEQ ID NO: 27 does not comprise SEQ ID NO: 23 (unsubstituted α chain constant region) |
| SEQ ID NO: 28 (4304 TCR1 β chain) (predicted sequence without N-terminal signal peptide) | X at position 171 is Ser |

In an embodiment of the invention, the substituted amino acid sequence includes the cysteine substitutions in the constant region of one or both of the α and β chains in combination with the substitution(s) of one, two, or three amino acids in the transmembrane (TM) domain of the constant region of the α chain with a hydrophobic amino acid (also referred to herein as "cysteine-substituted, LVL-modified TCR"). In this regard, the TCR is a cysteine-substituted, LVL-modified, chimeric TCR in which the native Thr48 of SEQ ID NO: 23 is substituted with Cys; one, two, or three of the native Ser112, Met114, and Gly115 of SEQ ID NO: 23 are, independently, substituted with Ala, Val, Leu, Ile, Pro, Phe, Met, or Trp; preferably with Leu, Ile, or Val; and the native Ser57 of SEQ ID NO: 24 is substituted include the substituted constant region in addition to any of the CDRs or variable regions described herein.

In an embodiment, the cysteine-substituted, LVL-modified TCR comprises a full-length α chain and a full-length β chain. Examples of cysteine-substituted, LVL-modified TCR α chain and β chain sequences are set forth in Tables 4 and 8. In an embodiment of the invention, the TCR comprises: (i) SEQ ID NO: 25, (ii) SEQ ID NO: 26, (iii) SEQ ID NO: 27, (iv) SEQ ID NO: 28, (v) SEQ ID NO: 29, (vi) SEQ ID NO: 30, (vii) SEQ ID NO: 31, (viii) SEQ ID NO: 32, (ix) both of SEQ ID NOs: 25 and 26, or (x) both of SEQ ID NOs: 27 and 28, (xi) both of SEQ ID NOs: 29 and 30, or (xii) both of SEQ ID NOs: 31 and 32, wherein all of SEQ ID NOs: 25-28 are as defined in Table 4.

TABLE 4

| SEQ ID NO: | Definitions of "X" |
| --- | --- |
| SEQ ID NO: 19 (constant region α chain) | X at position 48 is Cys; X at position 112 is Ser, Ala, Val, Leu, Ile, Pro, Phe, Met, or Trp; preferably wherein X at position 112 is Leu, Ile, or Val; especially preferably wherein X at position 112 is Leu; X at position 114 is Met, Ala, Val, Leu, Ile, Pro, Phe, or Trp; preferably wherein X at position 114 is Leu, Ile, or Val; especially preferably wherein X at position 114 is Ile; and X at position 115 is Gly, Ala, Val, Leu, Ile, Pro, Phe, Met, or Trp; preferably wherein X at position 115 is Leu, Ile, or Val; and especially preferably wherein X at position 115 is Val, wherein SEQ ID NO: 19 does not simultaneously comprise all of Ser at position 112, Met at position 114, and Gly at position 115. |
| SEQ ID NO: 20 (constant region β chain) | X at position 57 is Cys |
| SEQ ID NO: 25 (4304 TCR1 α chain) (with N-terminal signal peptide) | X at position 175 is Cys; X at position 239 is Ser, Ala, Val, Leu, Ile, Pro, Phe, Met, or Trp; preferably wherein X at position 239 is Leu, Ile, or Val; especially preferably wherein X at position 239 is Leu; X at position 241 is Met, Ala, Val, Leu, Ile, Pro, Phe, or Trp; preferably wherein X at position 241 is Leu, Ile, or Val; especially preferably wherein X at position 241 is Ile; and X at position 242 is Gly, Ala, Val, Leu, Ile, Pro, Phe, Met, or Trp; preferably wherein X at position 242 is Leu, Ile, or Val; and especially preferably wherein X at position 242 is Val, wherein SEQ ID NO: 25 does not simultaneously comprise all of Ser at position 239, Met at position 241, and Gly at position 242. |
| SEQ ID NO: 26 (4304 TCR1 β chain) (with N-terminal signal peptide) | X at position 186 is Cys |
| SEQ ID NO: 27 (4304 TCR1 α chain) (predicted sequence without N-terminal signal peptide) | X at position 156 is Cys; X at position 220 is Ser, Ala, Val, Leu, Ile, Pro, Phe, Met, or Trp; preferably wherein X at position 220 is Leu, Ile, or Val; especially preferably wherein X at position 220 is Leu; X at position 222 is Met, Ala, Val, Leu, Ile, Pro, Phe, or Trp; preferably wherein X at position 222 is Leu, Ile, or Val; especially preferably wherein X at position 222 is Ile; and X at position 223 is Gly, Ala, Val, Leu, Ile, Pro, Phe, Met, or Trp; preferably wherein X at position 223 is Leu, Ile, or Val; and especially preferably wherein X at position 223 is Val, wherein SEQ ID NO: 27 does not simultaneously comprise all of Ser at position 220, Met at position 222, and Gly at position 223. |
| SEQ ID NO: 28 (4304 TCR1 β chain) (predicted sequence without N-terminal signal peptide) | X at position 171 is Cys | with Cys. Preferably, all three of the native Ser112, Met114, and Gly115 of SEQ ID NO: 23 may, independently, be substituted with Ala, Val, Leu, Ile, Pro, Phe, Met, or Trp; preferably with Leu, Ile, or Val. In an embodiment of the invention, the cysteine-substituted, LVL-modified TCR comprises (i) SEQ ID NO: 19, (ii) SEQ ID NO: 20, or (iii) both of SEQ ID NOs: 19 and 20, wherein both of SEQ ID NOs: 19 and 20 are as defined in Table 4. The cysteine-substituted, LVL-modified TCRs of the invention may In an embodiment of the invention, the cysteine-substituted, LVL-modified TCR comprises (a) SEQ ID NO: 21 (a chain constant region of cysteine-substituted, LVL-modified TCR); (b) SEQ ID NO: 22 (β chain constant region of cysteine-substituted, LVL-modified TCR); or (c) both (a) and (b).

Also provided by the invention is a polypeptide comprising a functional portion of any of the TCRs described herein. The term "polypeptide," as used herein, includes oligopeptides and refers to a single chain of amino acids connected by one or more peptide bonds.

With respect to the inventive polypeptides, the functional portion can be any portion comprising contiguous amino acids of the TCR of which it is a part, provided that the functional portion specifically binds to G12V RAS. The term "functional portion," when used in reference to a TCR, refers to any part or fragment of the TCR of the invention, which part or fragment retains the biological activity of the TCR of which it is a part (the parent TCR). Functional portions encompass, for example, those parts of a TCR that retain the ability to specifically bind to G12V RAS (e.g., within the context of any of the HLA Class II molecules described herein), or detect, treat, or prevent cancer, to a similar extent, the same extent, or to a higher extent, as the parent TCR. In reference to the parent TCR, the functional portion can comprise, for instance, about 10%, about 25%, about 30%, about 50%, about 70%, about 80%, about 90%, about 95%, or more, of the parent TCR.

The functional portion can comprise additional amino acids at the amino or carboxy terminus of the portion, or at both termini, which additional amino acids are not found in the amino acid sequence of the parent TCR. Desirably, the additional amino acids do not interfere with the biological function of the functional portion, e.g., specifically binding to G12V RAS; and/or having the ability to detect cancer, treat or prevent cancer, etc. More desirably, the additional amino acids enhance the biological activity, as compared to the biological activity of the parent TCR.

The polypeptide can comprise a functional portion of either or both of the α and β chains of the TCRs of the invention, such as a functional portion comprising one or more of the CDR1, CDR2, and CDR3 of the variable region(s) of the α chain and/or β chain of a TCR of the invention. In an embodiment of the invention, the polypeptide can comprise the amino acid sequence of SEQ ID NO: 1 (CDR1 of α chain of 4304 TCR1), the amino acid sequence of SEQ ID NO: 2 (CDR2 of a chain of 4304 TCR1), the amino acid sequence of SEQ ID NO: 3 (CDR3 of α chain of 4304 TCR1), the amino acid sequence of SEQ ID NO: 4 (CDR1 of β chain of 4304 TCR1), the amino acid sequence of SEQ ID NO: 5 (CDR2 of β chain of 4304 TCR1), the amino acid sequence of SEQ ID NO: 6 (CDR3 of β chain of 4304 TCR1), or a combination thereof. In this regard, the inventive polypeptide can comprise any one or more of the amino acid sequences selected from the group consisting of SEQ ID NOs: 1-6. In an embodiment of the invention, the polypeptide comprises the amino acid sequences of: (a) all of SEQ ID NOs: 1-3, (b) all of SEQ ID NOs: 4-6, or (c) all of SEQ ID NOs: 1-6. In a preferred embodiment, the polypeptide comprises the amino acid sequences of all of SEQ ID NOs: 1-6.

In an embodiment of the invention, the inventive polypeptide can comprise, for instance, the variable region of the inventive TCR comprising a combination of the CDR regions set forth above. In this regard, the polypeptide can comprise the amino acid sequence of (i) SEQ ID NO: 7 (predicted sequence of variable region of α chain of 4304 TCR1 without N-terminal signal peptide); (ii) SEQ ID NO: 8 (predicted sequence of variable region of β chain of 4304 TCR1 without N-terminal signal peptide); (iii) SEQ ID NO: 9 (variable region of α chain of 4304 TCR1 with N-terminal signal peptide); (iv) SEQ ID NO: 10 (variable region of β chain of 4304 TCR1 with N-terminal signal peptide); (v) both of SEQ ID NOs: 7 and 8; or (vi) both of SEQ ID NOs: 9 and 10. Preferably, the polypeptide comprises the amino acid sequences of (i) both of SEQ ID NOs: 7 and 8 or (ii) both of SEQ ID NOs: 9 and 10.

In an embodiment of the invention, the inventive polypeptide can further comprise the constant region of the inventive TCR set forth above. In this regard, the polypeptide can further comprise the amino acid sequence of SEQ ID NO: 23 (WT murine constant region of α chain), SEQ ID NO: 24 (WT murine constant region of β chain), SEQ ID NO: 19 (substituted murine constant region of α chain), SEQ ID NO: 20 (substituted murine constant region of β chain), SEQ ID NO: 21 (α chain constant region of cysteine-substituted, LVL-modified TCR); SEQ ID NO: 22 (β chain constant region of cysteine-substituted, LVL-modified TCR); both SEQ ID NOs: 19 and 20, both SEQ ID NOs: 21 and 22, or both SEQ ID NOs: 23 and 24. Preferably, the polypeptide further comprises the amino acid sequences of both of SEQ ID NOs: 19 and 20, both of SEQ ID NO: 21 and 22, or both of SEQ ID NOs: 23 and 24 in combination with any of the CDR regions or variable regions described herein with respect to other aspects of the invention. In an embodiment of the invention, one or both of SEQ ID NOs: 19 and 20 of the polypeptide are as defined in any one of Tables 2-4.

In an embodiment of the invention, the inventive polypeptide can comprise the entire length of an α or β chain of the TCR described herein. In this regard, the inventive polypeptide can comprise the amino acid sequence of SEQ ID NO: 25, SEQ ID NO: 26, SEQ ID NO: 27, SEQ ID NO: 28, SEQ ID NO: 29, SEQ ID NO: 30, SEQ ID NO: 31, or SEQ ID NO: 32. Alternatively, the polypeptide of the invention can comprise both chains of the TCRs described herein. For example, the polypeptide may comprise both of SEQ ID NOs: 25-26, both of SEQ ID NOs: 27-28, SEQ ID NOs: 29-30, or both of SEQ ID NOs: 31-32.

For example, the polypeptide of the invention can comprise (a) an α chain comprising the amino acid sequence of SEQ ID NO: 25, wherein: (i) X at position 175 of SEQ ID NO: 25 is Thr or Cys; (ii) X at position 239 of SEQ ID NO: 25 is Ser, Ala, Val, Leu, Ile, Pro, Phe, Met, or Trp; (iii) X at position 241 of SEQ ID NO: 25 is Met, Ala, Val, Leu, Ile, Pro, Phe, or Trp; and (iv) X at position 242 of SEQ ID NO: 25 is Gly, Ala, Val, Leu, Ile, Pro, Phe, Met, or Trp; (b) a β chain comprising the amino acid sequence of SEQ ID NO: 26, wherein X at position 186 of SEQ ID NO: 26 is Ser or Cys; (c) both SEQ ID NOs: 25 and 26; (d) an α chain comprising the amino acid sequence of SEQ ID NO: 27, wherein: (i) X at position 156 of SEQ ID NO: 27 is Thr or Cys; (ii) X at position 220 of SEQ ID NO: 27 is Ser, Ala, Val, Leu, Ile, Pro, Phe, Met, or Trp; (iii) X at position 222 of SEQ ID NO: 27 is Met, Ala, Val, Leu, Ile, Pro, Phe, or Trp; and (iv) X at position 223 of SEQ ID NO: 27 is Gly, Ala, Val, Leu, Ile, Pro, Phe, Met, or Trp; (e) a β chain comprising the amino acid sequence of SEQ ID NO: 28, wherein X at position 171 of SEQ ID NO: 28 is Ser or Cys; (f) both SEQ ID NOs: 27 and 28; (g) SEQ ID NO: 29; (h) SEQ ID NO: 30; (i) SEQ ID NO: 31; (j) SEQ ID NO: 32; (k) both SEQ ID NOs: 29 and 30; or (l) both SEQ ID NOs: 31 and 32. In an embodiment of the invention, any one or more of SEQ ID NOs: 25-28 of the polypeptide are as defined in any one of Tables 2-4.

The invention further provides a protein comprising at least one of the polypeptides described herein. By "protein" is meant a molecule comprising one or more polypeptide chains.

In an embodiment, the protein of the invention can comprise a first polypeptide chain comprising the amino acid sequences of SEQ ID NOs: 1-3 and a second polypeptide chain comprising the amino acid sequences of SEQ ID NOs: 4-6.

In another embodiment of the invention, (i) the first polypeptide chain comprises the amino acid sequence of SEQ ID NO: 7 and the second polypeptide chain comprises the amino acid sequence of SEQ ID NO: 8 or (ii) the first polypeptide chain comprises the amino acid sequence of SEQ ID NO: 9 and the second polypeptide chain comprises the amino acid sequence of SEQ ID NO: 10.

The inventive protein may further comprise any of the constant regions described herein with respect to other aspects of the invention. In this regard, in an embodiment of the invention, (i) the first polypeptide chain may further comprise the amino acid sequence of SEQ ID NO: 19 and the second polypeptide chain may further comprise the amino acid sequence of SEQ ID NO: 20; (ii) the first polypeptide chain may further comprise the amino acid sequence of SEQ ID NO: 21 and the second polypeptide chain may further comprise the amino acid sequence of SEQ ID NO: 22; or (ii) the first polypeptide chain may further comprise the amino acid sequence of SEQ ID NO: 23 and the second polypeptide chain may further comprise the amino acid sequence of SEQ ID NO: 24. In an embodiment of the invention, one or both of SEQ ID NOs: 19 and 20 of the protein are as defined in any one of Tables 2-4.

Alternatively or additionally, (a) the first polypeptide chain comprises the amino acid sequence of SEQ ID NO: 25, wherein: (i) X at position 175 of SEQ ID NO: 25 is Thr or Cys; (ii) X at position 239 of SEQ ID NO: 25 is Ser, Ala, Val, Leu, Ile, Pro, Phe, Met, or Trp; (iii) X at position 241 of SEQ ID NO: 25 is Met, Ala, Val, Leu, Ile, Pro, Phe, or Trp; and (iv) X at position 242 of SEQ ID NO: 25 is Gly, Ala, Val, Leu, Ile, Pro, Phe, Met, or Trp; (b) the second polypeptide chain comprises the amino acid sequence of SEQ ID NO: 26, wherein X at position 186 of SEQ ID NO: 26 is Ser or Cys; (c) both (a) and (b); (d) the first polypeptide chain comprises the amino acid sequence of SEQ ID NO: 27, wherein: (i) X at position 156 of SEQ ID NO: 27 is Thr or Cys; (ii) X at position 220 of SEQ ID NO: 27 is Ser, Ala, Val, Leu, Ile, Pro, Phe, Met, or Trp; (iii) X at position 222 of SEQ ID NO: 27 is Met, Ala, Val, Leu, Ile, Pro, Phe, or Trp; and (iv) X at position 223 of SEQ ID NO: 27 is Gly, Ala, Val, Leu, Ile, Pro, Phe, Met, or Trp; (e) the second polypeptide chain comprises the amino acid sequence of SEQ ID NO: 28, wherein X at position 171 of SEQ ID NO: 28 is Ser or Cys; (f) both (d) and (e); (g) the first polypeptide chain comprises the amino acid sequence of SEQ ID NO: 29; (h) the second polypeptide chain comprises the amino acid sequence of SEQ ID NO: 30; (i) the first polypeptide chain comprises the amino acid sequence of SEQ ID NO: 31; (j) the second polypeptide chain comprises the amino acid sequence of SEQ ID NO: 32; (k) both (g) and (h); or (1) both (i) and (j). In an embodiment of the invention, one or more of SEQ ID NOs: 25-28 are as defined in any one of Tables 2-4.

The protein of the invention can be a TCR. Alternatively, if, for example, the protein comprises a single polypeptide chain comprising the amino acid sequences of both the TCR α and β chains, or if the first and/or second polypeptide chain(s) of the protein further comprise(s) other amino acid sequences, e.g., an amino acid sequence encoding an immunoglobulin or a portion thereof, then the inventive protein can be a fusion protein. In this regard, the invention also provides a fusion protein comprising at least one of the inventive polypeptides described herein along with at least one other polypeptide. The other polypeptide can exist as a separate polypeptide of the fusion protein, or can exist as a polypeptide, which is expressed in frame (in tandem) with one of the inventive polypeptides described herein. The other polypeptide can encode any peptidic or proteinaceous molecule, or a portion thereof, including, but not limited to an immunoglobulin, CD3, CD4, CD8, an MHC molecule, a CD1 molecule, e.g., CD1a, CD1b, CD1c, CD1d, etc.

The fusion protein can comprise one or more copies of the inventive polypeptide and/or one or more copies of the other polypeptide. For instance, the fusion protein can comprise 1, 2, 3, 4, 5, or more, copies of the inventive polypeptide and/or of the other polypeptide. Suitable methods of making fusion proteins are known in the art, and include, for example, recombinant methods.

In some embodiments of the invention, the TCRs, polypeptides, and proteins of the invention may be expressed as a single protein comprising a linker peptide linking the α chain and the β chain. In this regard, the TCRs, polypeptides, and proteins of the invention may further comprise a linker peptide. The linker peptide may advantageously facilitate the expression of a recombinant TCR, polypeptide, and/or protein in a host cell. The linker peptide may comprise any suitable amino acid sequence. The linker peptide may be a cleavable linker peptide. For example, the linker peptide may be a furin-SGSG-P2A linker peptide comprising the amino acid sequence of RAKRSGS-GATNFSLLKQAGDVEENPGP (SEQ ID NO: 33). Upon expression of the construct including the linker peptide by a host cell, the linker peptide may be cleaved, resulting in separated α and β chains. In an embodiment of the invention, the TCR, polypeptide, or protein may comprise an amino acid sequence comprising a full-length α chain, a full-length β chain, and a linker peptide positioned between the α and β chains.

The protein of the invention can be a recombinant antibody, or an antigen binding portion thereof, comprising at least one of the inventive polypeptides described herein. As used herein, "recombinant antibody" refers to a recombinant (e.g., genetically engineered) protein comprising at least one of the polypeptides of the invention and a polypeptide chain of an antibody, or an antigen binding portion thereof. The polypeptide of an antibody, or antigen binding portion thereof, can be a heavy chain, a light chain, a variable or constant region of a heavy or light chain, a single chain variable fragment (scFv), or an Fc, Fab, or F(ab)₂' fragment of an antibody, etc. The polypeptide chain of an antibody, or an antigen binding portion thereof, can exist as a separate polypeptide of the recombinant antibody. Alternatively, the polypeptide chain of an antibody, or an antigen binding portion thereof, can exist as a polypeptide, which is expressed in frame (in tandem) with the polypeptide of the invention. The polypeptide of an antibody, or an antigen binding portion thereof, can be a polypeptide of any antibody or any antibody fragment, including any of the antibodies and antibody fragments described herein.

Included in the scope of the invention are functional variants of the inventive TCRs, polypeptides, or proteins described herein. The term "functional variant," as used herein, refers to a TCR, polypeptide, or protein having substantial or significant sequence identity or similarity to a parent TCR, polypeptide, or protein, which functional variant retains the biological activity of the TCR, polypeptide, or protein of which it is a variant. Functional variants encompass, for example, those variants of the TCR, polypeptide, or protein described herein (the parent TCR, polypeptide, or protein) that retain the ability to specifically bind to the G12V RAS for which the parent TCR has antigenic specificity or to which the parent polypeptide or protein specifically binds, to a similar extent, the same extent, or to a higher extent, as the parent TCR, polypeptide, or protein. In reference to the parent TCR, polypeptide, or protein, the functional variant can, for instance, be at least about 30%, about 50%, about 75%, about 80%, about 90%, about 95%, about 96%, about 97%, about 98%, about 99% or more identical in amino acid sequence to the parent TCR, polypeptide, or protein, respectively.

The functional variant can, for example, comprise the amino acid sequence of the parent TCR, polypeptide, or protein with at least one conservative amino acid substitution. Conservative amino acid substitutions are known in the art, and include amino acid substitutions in which one amino acid having certain physical and/or chemical properties is exchanged for another amino acid that has the same chemical or physical properties. For instance, the conservative amino acid substitution can be an acidic amino acid substituted for another acidic amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Val, etc.), a basic amino acid substituted for another basic amino acid (Lys, Arg, etc.), an amino acid with a polar side chain substituted for another amino acid with a polar side chain (Asn, Cys, Gln, Ser, Thr, Tyr, etc.), etc.

Alternatively or additionally, the functional variants can comprise the amino acid sequence of the parent TCR, polypeptide, or protein with at least one non-conservative amino acid substitution. In this case, it is preferable for the non-conservative amino acid substitution to not interfere with or inhibit the biological activity of the functional variant. Preferably, the non-conservative amino acid substitution enhances the biological activity of the functional variant, such that the biological activity of the functional variant is increased as compared to the parent TCR, polypeptide, or protein.

The TCR, polypeptide, or protein can consist essentially of the specified amino acid sequence or sequences described herein, such that other components of the TCR, polypeptide, or protein, e.g., other amino acids, do not materially change the biological activity of the TCR, polypeptide, or protein. In this regard, the inventive TCR, polypeptide, or protein can, for example, consist essentially of the amino acid sequence of SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, both of SEQ ID NOs: 25 and 26, both of SEQ ID NOs: 27 and 28, SEQ ID NOs: 29 and 30, or both of SEQ ID NOs: 31 and 32. Also, for instance, the inventive TCRs, polypeptides, or proteins can consist essentially of the amino acid sequence(s) of (i) SEQ ID NO: 7, (ii) SEQ ID NO: 8, (iii) SEQ ID NO: 9, (iv) SEQ ID NO: 10, (v) both of SEQ ID NOs: 7 and 8, or (vi) both of SEQ ID NOs: 9 and 10. Furthermore, the inventive TCRs, polypeptides, or proteins can consist essentially of the amino acid sequences of (a) all of SEQ ID NOs: 1-3, (b) all of SEQ ID NOs: 4-6, or (c) all of SEQ ID NOs: 1-6.

The TCRs, polypeptides, and proteins of the invention can be of any length, i.e., can comprise any number of amino acids, provided that the TCRs, polypeptides, or proteins retain their biological activity, e.g., the ability to specifically bind to G12V RAS; detect cancer in a mammal; or treat or prevent cancer in a mammal, etc. For example, the polypeptide can be in the range of from about 50 to about 5000 amino acids long, such as about 50, about 70, about 75, about 100, about 125, about 150, about 175, about 200, about 300, about 400, about 500, about 600, about 700, about 800, about 900, about 1000 or more amino acids in length. In this regard, the polypeptides of the invention also include oligopeptides.

The TCRs, polypeptides, and proteins of the invention can comprise synthetic amino acids in place of one or more naturally-occurring amino acids. Such synthetic amino acids are known in the art, and include, for example, aminocyclohexane carboxylic acid, norleucine, α-amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocycloheptane carboxylic acid, α-(2-amino-2-norbornane)-carboxylic acid, α,γ-diaminobutyric acid, α,β-diaminopropionic acid, homophenylalanine, and α-tert-butylglycine.

The TCRs, polypeptides, and proteins of the invention can be glycosylated, amidated, carboxylated, phosphorylated, esterified, N-acylated, cyclized via, e.g., a disulfide bridge, or converted into an acid addition salt and/or optionally dimerized or polymerized, or conjugated.

The TCR, polypeptide, and/or protein of the invention can be obtained by methods known in the art such as, for example, de novo synthesis. Also, polypeptides and proteins can be recombinantly produced using the nucleic acids described herein using standard recombinant methods. See, for instance, Green and Sambrook, *Molecular Cloning: A Laboratory Manual*, 4$^{th}$ ed., Cold Spring Harbor Press, Cold Spring Harbor, NY. (2012). Alternatively, the TCRs, polypeptides, and/or proteins described herein can be commercially synthesized by companies, such as Peptide Technologies Corp. (Gaithersburg, MD) GenScript (Piscataway, NJ), and RayBiotech Life (Peachtree Corners, GA). In this respect, the inventive TCRs, polypeptides, and proteins can be synthetic, recombinant, isolated, and/or purified. An embodiment of the invention provides an isolated or purified TCR, polypeptide, or protein encoded by any of the nucleic acids or vectors described herein with respect to other aspects of the invention. Another embodiment of the invention provides an isolated or purified TCR, polypeptide, or protein that results from expression of any of the nucleic acids or vectors described herein with respect to other aspects of the invention in a cell. Still another embodiment of the invention provides a method of producing any of the TCRs, polypeptides, or proteins described herein, the method comprising culturing any of the host cells or populations of host cells described herein so that the TCR, polypeptide, or protein is produced.

Included in the scope of the invention are conjugates, e.g., bioconjugates, comprising any of the inventive TCRs, polypeptides, or proteins (including any of the functional portions or variants thereof), nucleic acids, recombinant expression vectors, host cells, populations of host cells, or antibodies, or antigen binding portions thereof. Conjugates, as well as methods of synthesizing conjugates in general, are known in the art.

An embodiment of the invention provides a nucleic acid comprising a nucleotide sequence encoding any of the TCRs, polypeptides, or proteins described herein. "Nucleic acid," as used herein, includes "polynucleotide," "oligonucleotide," and "nucleic acid molecule," and generally means a polymer of DNA or RNA, which can be single-stranded or double-stranded, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. In an embodiment, the nucleic acid comprises complementary DNA (cDNA). It is generally preferred that the nucleic acid does not comprise any insertions, deletions, inversions, and/or substitutions. However, it may be suitable in some instances, as discussed herein, for the nucleic acid to comprise one or more insertions, deletions, inversions, and/or substitutions.

Preferably, the nucleic acids of the invention are recombinant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication.

In an embodiment of the invention, the nucleic acid comprises the nucleotide sequence of SEQ ID NO: 38 (encodes both α and β chain of 4304 TCR1 separated by cleavable linker peptide), SEQ ID NO: 39 (encodes α chain variable region of 4304 TCR1), SEQ ID NO: 40 (encodes β chain variable region of 4304 TCR1), or both SEQ ID NO: 39 and 40.

The nucleic acids can be constructed based on chemical synthesis and/or enzymatic ligation reactions using procedures known in the art. See, for example, Green and Sambrook et al., supra. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, β-D-galactosylqueosine, inosine, $N^6$-isopentenyladenine, 1-methylguanine, 1-methylinosine, 2,2-dimethylguanine, 2-methyladenine, 2-methylguanine, 3-methylcytosine, 5-methylcytosine, $N^6$-substituted adenine, 7-methylguanine, 5-methylaminomethyluracil, 5-methoxyaminomethyl-2-thiouracil, β-D-mannosylqueosine, 5'-methoxycarboxymethyluracil, 5-methoxyuracil, 2-methylthio-$N^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the invention can be purchased from any of a variety of commercial entities.

The nucleic acid can comprise any nucleotide sequence which encodes any of the TCRs, polypeptides, or proteins described herein. In an embodiment of the invention, the nucleic acid comprises a codon-optimized nucleotide sequence encoding any of the TCRs, polypeptides, or proteins described herein. Without being bound to any particular theory or mechanism, it is believed that codon optimization of the nucleotide sequence increases the translation efficiency of the mRNA transcripts. Codon optimization of the nucleotide sequence may involve substituting a native codon for another codon that encodes the same amino acid, but can be translated by tRNA that is more readily available within a cell, thus increasing translation efficiency. Optimization of the nucleotide sequence may also reduce secondary mRNA structures that would interfere with translation, thus increasing translation efficiency.

The invention also provides a nucleic acid comprising a nucleotide sequence which is complementary to the nucleotide sequence of any of the nucleic acids described herein or a nucleotide sequence which hybridizes under stringent conditions to the nucleotide sequence of any of the nucleic acids described herein.

The nucleotide sequence which hybridizes under stringent conditions preferably hybridizes under high stringency conditions. By "high stringency conditions" is meant that the nucleotide sequence specifically hybridizes to a target sequence (the nucleotide sequence of any of the nucleic acids described herein) in an amount that is detectably stronger than non-specific hybridization. High stringency conditions include conditions which would distinguish a polynucleotide with an exact complementary sequence, or one containing only a few scattered mismatches from a random sequence that happened to have a few small regions (e.g., 3-10 bases) that matched the nucleotide sequence. Such small regions of complementarity are more easily melted than a full-length complement of 14-17 or more bases, and high stringency hybridization makes them easily distinguishable. Relatively high stringency conditions would include, for example, low salt and/or high temperature conditions, such as provided by about 0.02-0.1 M NaCl or the equivalent, at temperatures of about 50-70° C. Such high stringency conditions tolerate little, if any, mismatch between the nucleotide sequence and the template or target strand, and are particularly suitable for detecting expression of any of the inventive TCRs. It is generally appreciated that conditions can be rendered more stringent by the addition of increasing amounts of formamide.

An embodiment of the invention also provides a nucleic acid comprising a nucleotide sequence that is at least about 70% or more, e.g., about 80%, about 90%, about 91%, about 92%, about 93%, about 94%, about 95%, about 96%, about 97%, about 98%, or about 99% identical to any of the nucleic acids described herein. In this regard, the nucleic acid may consist essentially of any of the nucleotide sequences described herein.

An embodiment of the invention provides an isolated or purified nucleic acid comprising, from 5' to 3', a first nucleic acid sequence and a second nucleotide sequence, wherein the first and second nucleotide sequence, respectively, encode the amino sequences of SEQ ID NOs: 7 and 8; 8 and 7; 9 and 10; 10 and 9; 25 and 26; 26 and 25; 27 and 28; 28 and 27; 29 and 30; 30 and 29; 31 and 32; or 32 and 31.

In an embodiment of the invention, the isolated or purified nucleic acid further comprises a third nucleotide sequence interposed between the first and second nucleotide sequence, wherein the third nucleotide sequence encodes a cleavable linker peptide. In an embodiment of the invention, the cleavable linker peptide comprises the amino acid sequence of RAKRSGSGATNFSLLKQAGDVEENPGP (SEQ ID NO: 33).

The nucleic acids of the invention can be incorporated into a recombinant expression vector. In this regard, the invention provides a recombinant expression vector comprising any of the nucleic acids of the invention. In an embodiment of the invention, the recombinant expression vector comprises a nucleotide sequence encoding the α chain, the β chain, and linker peptide.

For purposes herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors of the invention are not naturally-occurring as a whole. However, parts of the vectors can be naturally-occurring. The inventive recombinant expression vectors can comprise any type of nucleotide, including, but not limited to DNA and RNA, which can be single-stranded or double-stranded, synthesized or obtained in part from natural sources, and which can contain natural, non-natural or altered nucleotides. The recombinant expression vectors can comprise naturally-occurring, non-naturally-occurring internucleotide linkages, or both types of linkages. Preferably, the non-naturally occurring or altered nucleotides or internucleotide linkages do not hinder the transcription or replication of the vector.

The recombinant expression vector of the invention can be any suitable recombinant expression vector, and can be used to transform or transfect any suitable host cell. Suitable vectors include those designed for propagation and expansion or for expression or both, such as plasmids and viruses. The vector can be selected from the group consisting of the pUC series (Fermentas Life Sciences), the pBluescript series (Stratagene, LaJolla, CA), the pET series (Novagen, Madison, WI), the pGEX series (Pharmacia Biotech, Uppsala, Sweden), and the pEX series (Clontech, Palo Alto, CA). Bacteriophage vectors, such as λGT10, λGT11, λZapII (Stratagene), λEMBL4, and λNM1149, also can be used. Examples of plant expression vectors include pBI01, pBI101.2, pBI101.3, pBI121 and pBIN19 (Clontech). Examples of animal expression vectors include pEUK-Cl, pMAM and pMAMneo (Clontech). Preferably, the recombinant expression vector is a viral vector, e.g., a retroviral vector. In an especially preferred embodiment, the recombinant expression vector is an MSGV1 vector. In an embodiment of the invention, the recombinant expression vector is a transposon or a lentiviral vector.

The recombinant expression vectors of the invention can be prepared using standard recombinant DNA techniques described in, for example, Green and Sambrook et al., supra. Constructs of expression vectors, which are circular or linear, can be prepared to contain a replication system functional in a prokaryotic or eukaryotic host cell. Replication systems can be derived, e.g., from ColEl, 2μ plasmid, λ, SV40, bovine papillomavirus, and the like.

Desirably, the recombinant expression vector comprises regulatory sequences, such as transcription and translation initiation and termination codons, which are specific to the type of host cell (e.g., bacterium, fungus, plant, or animal) into which the vector is to be introduced, as appropriate and taking into consideration whether the vector is DNA- or RNA-based.

The recombinant expression vector can include one or more marker genes, which allow for selection of transformed or transfected host cells. Marker genes include biocide resistance, e.g., resistance to antibiotics, heavy metals, etc., complementation in an auxotrophic host cell to provide prototrophy, and the like. Suitable marker genes for the inventive expression vectors include, for instance, neomycin/G418 resistance genes, hygromycin resistance genes, histidinol resistance genes, tetracycline resistance genes, and ampicillin resistance genes.

The recombinant expression vector can comprise a native or nonnative promoter operably linked to the nucleotide sequence encoding the TCR, polypeptide, or protein, or to the nucleotide sequence which is complementary to or which hybridizes to the nucleotide sequence encoding the TCR, polypeptide, or protein. The selection of promoters, e.g., strong, weak, inducible, tissue-specific and developmental-specific, is within the ordinary skill of the artisan. Similarly, the combining of a nucleotide sequence with a promoter is also within the skill of the artisan. The promoter can be a non-viral promoter or a viral promoter, e.g., a cytomegalovirus (CMV) promoter, an SV40 promoter, an RSV promoter, and a promoter found in the long-terminal repeat of the murine stem cell virus.

The inventive recombinant expression vectors can be designed for either transient expression, for stable expression, or for both. Also, the recombinant expression vectors can be made for constitutive expression or for inducible expression.

Further, the recombinant expression vectors can be made to include a suicide gene. As used herein, the term "suicide gene" refers to a gene that causes the cell expressing the suicide gene to die. The suicide gene can be a gene that confers sensitivity to an agent, e.g., a drug, upon the cell in which the gene is expressed, and causes the cell to die when the cell is contacted with or exposed to the agent. Suicide genes are known in the art and include, for example, the Herpes Simplex Virus (HSV) thymidine kinase (TK) gene, cytosine deaminase, purine nucleoside phosphorylase, nitroreductase, and the inducible caspase 9 gene system.

Another embodiment of the invention further provides a host cell comprising any of the nucleic acids or recombinant expression vectors described herein. As used herein, the term "host cell" refers to any type of cell that can contain the inventive recombinant expression vector. The host cell can be a eukaryotic cell, e.g., plant, animal, fungi, or algae, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. Suitable host cells are known in the art and include, for instance, DH5α E. coli cells, Chinese hamster ovarian cells, monkey VERO cells, COS cells, HEK293 cells, and the like. For purposes of amplifying or replicating the recombinant expression vector, the host cell is preferably a prokaryotic cell, e.g., a DH5α cell. For purposes of producing a recombinant TCR, polypeptide, or protein, the host cell is preferably a mammalian cell. Most preferably, the host cell is a human cell. While the host cell can be of any cell type, can originate from any type of tissue, and can be of any developmental stage, the host cell preferably is a peripheral blood lymphocyte (PBL) or a peripheral blood mononuclear cell (PBMC). More preferably, the host cell is a T cell. In an embodiment of the invention, the host cell is a human lymphocyte. In another embodiment of the invention, the host cell is selected from the group consisting of a T cell, a natural killer T (NKT) cell, an invariant natural killer T (iNKT) cell, and a natural killer (NK) cell. Still another embodiment of the invention provides a method of producing a host cell expressing a TCR that has antigenic specificity for the peptide of MTEYKLVVVGAVGVGK-SALTIQLI (SEQ ID NO: 34), the method comprising contacting a cell with any of the vectors described herein under conditions that allow introduction of the vector into the cell.

For purposes herein, the T cell can be any T cell, such as a cultured T cell, e.g., a primary T cell, or a T cell from a cultured T cell line, e.g., Jurkat, SupT1, etc., or a T cell obtained from a mammal. If obtained from a mammal, the T cell can be obtained from numerous sources, including but not limited to blood, bone marrow, lymph node, the thymus, or other tissues or fluids. T cells can also be enriched for or purified. Preferably, the T cell is a human T cell. The T cell can be any type of T cell and can be of any developmental stage, including but not limited to, CD4$^+$/CD8$^+$ double positive T cells, CD4$^+$ helper T cells, e.g., Th$_1$ and Th$_2$ cells, CD4$^+$ T cells, CD8$^+$ T cells (e.g., cytotoxic T cells), tumor infiltrating lymphocytes (TILs), memory T cells (e.g., central memory T cells and effector memory T cells), naïve T cells, and the like.

Also provided by the invention is a population of cells comprising at least one host cell described herein. The population of cells can be a heterogeneous population comprising the host cell comprising any of the recombinant expression vectors described, in addition to at least one other cell, e.g., a host cell (e.g., a T cell), which does not comprise any of the recombinant expression vectors, or a cell other than a T cell, e.g., a B cell, a macrophage, a neutrophil, an erythrocyte, a hepatocyte, an endothelial cell, an epithelial cells, a muscle cell, a brain cell, etc. Alternatively, the population of cells can be a substantially homogeneous population, in which the population comprises mainly of host cells (e.g., consisting essentially of) comprising the recombinant expression vector. The population also can be a clonal population of cells, in which all cells of the population are clones of a single host cell comprising a recombinant expression vector, such that all cells of the population comprise the recombinant expression vector. In one embodiment of the invention, the population of cells is a clonal population comprising host cells comprising a recombinant expression vector as described herein.

In an embodiment of the invention, the numbers of cells in the population may be rapidly expanded. Expansion of the numbers of T cells can be accomplished by any of a number of methods as are known in the art as described in, for example, U.S. Pat. Nos. 8,034,334; 8,383,099; U.S. Patent Application Publication No. 2012/0244133; Dudley et al., *J. Immunother.*, 26:332-42 (2003); and Riddell et al., *J. Immunol. Methods,* 128:189-201 (1990). In an embodiment, expansion of the numbers of T cells is carried out by culturing the T cells with OKT3 antibody, IL-2, and feeder PBMC (e.g., irradiated allogeneic PBMC).

The inventive TCRs, polypeptides, proteins, nucleic acids, recombinant expression vectors, and host cells (including populations thereof), can be isolated and/or purified. The term "isolated," as used herein, means having been removed from its natural environment. The term "purified," as used herein, means having been increased in purity, wherein "purity" is a relative term, and not to be necessarily construed as absolute purity. For example, the purity can be at least about 50%, can be greater than about 60%, about 70%, about 80%, about 90%, about 95%, or can be about 100%.

The inventive TCRs, polypeptides, proteins, nucleic acids, recombinant expression vectors, and host cells (including populations thereof), all of which are collectively referred to as "inventive TCR materials" hereinafter, can be formulated into a composition, such as a pharmaceutical composition. In this regard, the invention provides a pharmaceutical composition comprising any of the TCRs, polypeptides, proteins, nucleic acids, expression vectors, and host cells (including populations thereof), described herein, and a pharmaceutically acceptable carrier. The inventive pharmaceutical compositions containing any of the inventive TCR materials can comprise more than one inventive TCR material, e.g., a polypeptide and a nucleic acid, or two or more different TCRs. Alternatively, the pharmaceutical composition can comprise an inventive TCR material in combination with another pharmaceutically active agent(s) or drug(s), such as a chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc.

Preferably, the carrier is a pharmaceutically acceptable carrier. With respect to pharmaceutical compositions, the carrier can be any of those conventionally used for the particular inventive TCR material under consideration. Methods for preparing administrable compositions are known or apparent to those skilled in the art and are described in more detail in, for example, *Remington: The Science and Practice of Pharmacy,* 22$^{nd}$ Ed., Pharmaceutical Press (2012). It is preferred that the pharmaceutically acceptable carrier be one which has no detrimental side effects or toxicity under the conditions of use.

The choice of carrier will be determined in part by the particular inventive TCR material, as well as by the particular method used to administer the inventive TCR material. Accordingly, there are a variety of suitable formulations of the pharmaceutical composition of the invention. Suitable formulations may include any of those for parenteral, subcutaneous, intravenous, intramuscular, intraarterial, intrathecal, intratumoral, or interperitoneal administration. More than one route can be used to administer the inventive TCR materials, and in certain instances, a particular route can provide a more immediate and more effective response than another route.

Preferably, the inventive TCR material is administered by injection, e.g., intravenously. When the inventive TCR material is a host cell (or population thereof) expressing the inventive TCR, the pharmaceutically acceptable carrier for the cells for injection may include any isotonic carrier such as, for example, normal saline (about 0.90% w/v of NaCl in water, about 300 mOsm/L NaCl in water, or about 9.0 g NaCl per liter of water), NORMOSOL R electrolyte solution (Abbott, Chicago, IL), PLASMA-LYTE A (Baxter, Deerfield, IL), about 5% dextrose in water, or Ringer's lactate. In an embodiment, the pharmaceutically acceptable carrier is supplemented with human serum albumen.

For purposes of the invention, the amount or dose (e.g., numbers of cells when the inventive TCR material is one or more cells) of the inventive TCR material administered should be sufficient to effect, e.g., a therapeutic or prophylactic response, in the subject or animal over a reasonable time frame. For example, the dose of the inventive TCR material should be sufficient to bind to a cancer antigen (e.g., G12V RAS), or detect, treat or prevent cancer in a period of from about 2 hours or longer, e.g., 12 to 24 or more hours, from the time of administration. In certain embodiments, the time period could be even longer. The dose will be determined by the efficacy of the particular inventive TCR material and the condition of the animal (e.g., human), as well as the body weight of the animal (e.g., human) to be treated.

Many assays for determining an administered dose are known in the art. For purposes of the invention, an assay, which comprises comparing the extent to which target cells are lysed or IFN-γ is secreted by T cells expressing the inventive TCR, polypeptide, or protein upon administration of a given dose of such T cells to a mammal among a set of mammals of which each is given a different dose of the T cells, could be used to determine a starting dose to be administered to a mammal. The extent to which target cells are lysed or IFN-γ is secreted upon administration of a certain dose can be assayed by methods known in the art.

The dose of the inventive TCR material also will be determined by the existence, nature and extent of any adverse side effects that might accompany the administration of a particular inventive TCR material. Typically, the attending physician will decide the dosage of the inventive TCR material with which to treat each individual patient, taking into consideration a variety of factors, such as age, body weight, general health, diet, sex, inventive TCR material to be administered, route of administration, and the severity of the cancer being treated. In an embodiment in which the inventive TCR material is a population of cells, the number of cells administered per infusion may vary, e.g., from about $1 \times 10^6$ to about $1 \times 10^{12}$ cells or more. In certain embodiments, fewer than $1 \times 10^6$ cells may be administered.

One of ordinary skill in the art will readily appreciate that the inventive TCR materials of the invention can be modified in any number of ways, such that the therapeutic or prophylactic efficacy of the inventive TCR materials is increased through the modification. For instance, the inventive TCR materials can be conjugated either directly or indirectly through a bridge to a chemotherapeutic agent. The practice of conjugating compounds to a chemotherapeutic agent is known in the art. One of ordinary skill in the art recognizes that sites on the inventive TCR materials, which are not necessary for the function of the inventive TCR materials, are suitable sites for attaching a bridge and/or a chemotherapeutic agent, provided that the bridge and/or chemotherapeutic agent, once attached to the inventive TCR materials, do(es) not interfere with the function of the inventive TCR materials, i.e., the ability to bind to G12V RAS or to detect, treat, or prevent cancer.

It is contemplated that the inventive pharmaceutical compositions, TCRs, polypeptides, proteins, nucleic acids, recombinant expression vectors, host cells, and populations of cells can be used in methods of treating or preventing cancer. Without being bound to a particular theory, the inventive TCRs are believed to bind specifically to G12V RAS, such that the TCR (or related inventive polypeptide or protein), when expressed by a cell, is able to mediate an immune response against a target cell expressing G12V RAS. In this regard, an embodiment of the invention provides a method of treating or preventing cancer in a mammal, comprising administering to the mammal any of the pharmaceutical compositions, TCRs, polypeptides, or proteins described herein, any nucleic acid or recombinant expression vector comprising a nucleotide sequence encoding any of the TCRs, polypeptides, proteins described herein, or any host cell or population of cells comprising a recombinant vector which encodes any of the TCRs, polypeptides, or proteins described herein, in an amount effective to treat or prevent cancer in the mammal.

An embodiment of the invention provides a method of inducing an immune response against a cancer in a mammal, comprising administering to the mammal any of the pharmaceutical compositions, TCRs, polypeptides, or proteins described herein, any nucleic acid or recombinant expression vector comprising a nucleotide sequence encoding any of the TCRs, polypeptides, or proteins described herein, or any host cell or population of cells comprising a recombinant vector which encodes any of the TCRs, polypeptides, or proteins described herein, in an amount effective to induce an immune response against the cancer in the mammal.

An embodiment of the invention provides any of the pharmaceutical compositions, TCRs, polypeptides, or proteins described herein, any nucleic acid or recombinant expression vector comprising a nucleotide sequence encoding any of the TCRs, polypeptides, proteins described herein, or any host cell or population of cells comprising a recombinant vector which encodes any of the TCRs, polypeptides, or proteins described herein, for use in the treatment or prevention of cancer in a mammal.

An embodiment of the invention provides any of the pharmaceutical compositions, TCRs, polypeptides, or proteins described herein, any nucleic acid or recombinant expression vector comprising a nucleotide sequence encoding any of the TCRs, polypeptides, or proteins described herein, or any host cell or population of cells comprising a recombinant vector which encodes any of the TCRs, polypeptides, or proteins described herein, for use in inducing an immune response against a cancer in a mammal.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of cancer in a mammal. Furthermore, the treatment or prevention provided by the inventive method can include treatment or prevention of one or more conditions or symptoms of the cancer being treated or prevented. For example, treatment or prevention can include promoting the regression of a tumor. Also, for purposes herein, "prevention" can encompass delaying the onset of the cancer, or a symptom or condition thereof. Alternatively or additionally, "prevention" may encompass preventing or delaying the recurrence of cancer, or a symptom or condition thereof.

Also provided is a method of detecting the presence of cancer in a mammal. The method comprises (i) contacting a sample comprising one or more cells from the mammal with any of the inventive TCRs, polypeptides, proteins, nucleic acids, recombinant expression vectors, host cells, populations of cells, or pharmaceutical compositions described herein, thereby forming a complex, and (ii) detecting the complex, wherein detection of the complex is indicative of the presence of cancer in the mammal.

With respect to the inventive method of detecting cancer in a mammal, the sample of cells can be a sample comprising whole cells, lysates thereof, or a fraction of the whole cell lysates, e.g., a nuclear or cytoplasmic fraction, a whole protein fraction, or a nucleic acid fraction.

For purposes of the inventive method of detecting cancer, the contacting can take place in vitro or in vivo with respect to the mammal. Preferably, the contacting is in vitro.

Also, detection of the complex can occur through any number of ways known in the art. For instance, the inventive TCRs, polypeptides, proteins, nucleic acids, recombinant expression vectors, host cells, or populations of cells, described herein, can be labeled with a detectable label such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

For purposes of the inventive methods, wherein host cells or populations of cells are administered, the cells can be cells that are allogeneic or autologous to the mammal. Preferably, the cells are autologous to the mammal.

With respect to the inventive methods, the cancer can be any cancer, including any of acute lymphocytic cancer, acute myeloid leukemia, alveolar rhabdomyosarcoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vagina, cancer of the vulva, chronic lymphocytic leukemia, chronic myeloid cancer, colon cancer, colorectal cancer, endometrial cancer, esophageal cancer, uterine cervical cancer, gastrointestinal carcinoid tumor, glioma, Hodgkin lymphoma, hypopharynx cancer, kidney cancer, larynx cancer, liver cancer, lung cancer, malignant mesothelioma, melanoma, multiple myeloma, nasopharynx cancer, non-Hodgkin lymphoma, cancer of the oropharynx, ovarian cancer, cancer of the penis, pancreatic cancer, peritoneum, omentum, and mesentery cancer, pharynx cancer, prostate cancer, rectal cancer, renal cancer, skin cancer, small intestine cancer, soft tissue cancer, stomach cancer, testicular cancer, thyroid cancer, cancer of the uterus, ureter cancer, and urinary bladder cancer. A preferred cancer is pancreatic, colorectal, lung, endometrial, ovarian, or prostate cancer. Preferably, the lung cancer is lung adenocarcinoma, the ovarian cancer is epithelial ovarian cancer, and the pancreatic cancer is pancreatic adenocarcinoma. In an embodiment of the invention, the cancer expresses a mutated human RAS amino acid sequence with a substitution of glycine at position 12 with valine, wherein the mutated human RAS amino acid sequence is a mutated human KRAS, a mutated human HRAS, or a mutated human NRAS amino acid sequence, and wherein position 12 is defined by reference to the WT human KRAS, WT human HRAS, or WT human NRAS protein, respectively. The mutated human KRAS, mutated human HRAS, and mutated human NRAS expressed by the cancer may be as described herein with respect to other aspects of the invention.

The mammal referred to in the inventive methods can be any mammal. As used herein, the term "mammal" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

The following examples further illustrate the invention but, of course, should not be construed as in any way limiting its scope.

Example 1

This example demonstrates the isolation of an anti-G12V RAS TCR from the TIL of colorectal cancer patient 4304.

TIL from colorectal cancer patient 4304 were independently screened for reactivity against multiple different neoantigens expressed by the patient. Reactivity was observed against G12V, as described below. TIL from tumor fragments (numbered F2, F4, F5, F23, and F24) from patient 4304 were co-cultured with dendritic cells (DC). The DCs had been (i) independently pulsed with one of eight different pools of 24-mer peptides (peptide pool numbers 1-8 (PP 1 to PP 8)) or (ii) independently transduced with one of five different tandem minigene (TMG) constructs. Each peptide of a pool comprised a different neoantigen expressed by the patient. One TMG construct encoded multiple different irrelevant peptides in tandem. Each of the other four TMG constructs encoded multiple different 24-mer peptides comprising a neontigen expressed by the patient in tandem. The TIL were co-cultured with DC treated with dimethyl sulfoxide (DMSO) as a negative control. TIL were treated with phorbol myristate acetate (PMA) as a positive control.

Reactivity was tested by IFNγ-secretion using enzyme-linked immunospot (ELISpot) assay. The results for tumor fragment F4 are presented in Table 5. Reactive cells were observed with TIL co-cultured with DCs which had been pulsed with PP 3. To determine which peptide of PP 3 provided reactivity, the TIL were independently co-cultured with DCs that were separately pulsed with each peptide from PP 3. The results are presented in Table 6. Reactive cells were observed by co-culture of the TIL with DCs which had been pulsed with the G12V 24-mer peptide.

TABLE 5

| Peptide pool (PP) No. | Number of positive spots measured by ELISpot | Tandem minigene (TMG) No. | Number of positive spots measured by ELISpot |
|---|---|---|---|
| PP 1 | 17 | TMG 1 | 19 |
| PP 2 | ~26 | TMG 2 | 2 |
| PP 3 | ~158 | TMG 3 | 3 |
| PP4 | ~80 | TMG 4 | 3 |
| PP 5 | 18 | Irrelevant TMG (Control) | 3 |
| PP 6 | ~18 | DMSO (Control) | ~15 |
| PP 7 | ~17 | Media (Control) | 1 |
| PP 8 | ~30 | PMA/ionomycin (Control) | ~118 |

TABLE 6

| Name of Peptide | Number of positive spots measured by ELISpot | Name of Peptide | Number of positive spots measured by ELISpot |
|---|---|---|---|
| LRP5 | ~186 | ACTC1 | ~317 |
| KSR2 | ~86 | ADAMTS7 | ~241 |
| PXMP2 | ~145 | SCNN1G | ~185 |
| KRAS | 909 | DMSO (Control) | 54 |
| ARID2 | ~373 | Media (Control) | 7 |
| IL25 | ~349 | Blank plate (Control) | 24 |
| FLRT2 | ~257 | Blank plate (Control) | 16 |
| FAM189A1 | ~178 | PMA/ionomycin (Control) | ~697 |

Positive cells were re-stimulated and sorted by 4-1BB upregulation into 96 well plates for single-cell T-cell receptor (TCR) sequencing. A TCR was found, namely 4304 TCR1 (TRBV29-1*01/TRBJ1-2*01/TRBD2*01/TRAV16*01).

The sequences of the TCR alpha and beta chain variable regions were identified by single-cell TCR sequencing. The amino acid sequences of the alpha and beta chain variable regions are shown in Table 7. The CDRs are underlined. The N-terminal signal peptides are in bold font.

TABLE 7

| TCR Name | TCR chain | Amino acid sequence |
|---|---|---|
| 4304 TCR1 | Variable α (Predicted sequence without N-terminal signal peptide) | AQRVTQPEKLLSVFKGAPVELKCNYSYSGSPELFWYVQYSRQ RLQLLLRHISRESIKGFTADLNKGETSFHLKKPFAQEEDSAMY YCALLQGAQKLVFGQGTRLTINP (SEQ ID NO: 7) |
| | Variable β (Predicted sequence without N-terminal signal peptide) | SAVISQKPSRDICQRGTSLTIQCQVDSQVTMMFWYRQQPGQSL TLIATANQGSEATYESGFVIDKFPISRPNLTFSTLTVSNMSPE DSSIYLCSVESGQDYGYTFGSGTRLTVV (SEQ ID NO: 8) |
| | Variable α (With N-terminal signal peptide) | MKPTLISVLVIIFILRGTRAQRVTQPEKLLSVFKGAPVELKCN YSYSGSPELFWYVQYSRQRLQLLLRHISRESIKGFTADLNKGE TSFHLKKPFAQEEDSAMYYCALLQGAQKLVFGQGTRLTINP (SEQ ID NO: 9) |
| | Variable β (With N-terminal signal peptide) | MASLLLLLLGLGSVFSAVISQKPSRDICQRGTSLTIQCQVDSQ VTMMFWYRQQPGQSLTLIATANQGSEATYESGFVIDKFPISRP NLTFSTLTVSNMSPEDSSIYLCSVESGQDYGYTFGSGTRLTVV (SEQ ID NO: 10) |

Example 2

This example demonstrates the construction of a retroviral vector encoding the TCR of Example 1.

Nucleotide sequences encoding the variable regions of the α and β chains of the 4304 TCR1 of Table 7 were obtained and codon optimized. The TCRβ VDJ regions were fused to the mouse TCRβ constant chain. The TCRα VJ regions were fused to the mouse TCRα constant chain. Without being bound to a particular theory or mechanism, it is believed that replacing the constant regions of the human TCRα and TCRβ chains with the corresponding murine constant regions improves TCR expression and functionality (Cohen et al., *Cancer Res.*, 66(17): 8878-86 (2006)).

In addition, the murine TCRα and TCRβ constant chains were cysteine-modified. Transmembrane hydrophobic mutations were introduced into the murine TCRα constant chain. Without being bound to a particular theory or mechanism, it is believed that these modifications result in preferential pairing of the introduced TCR chains and enhanced TCR surface expression and functionality (Cohen et al., *Cancer Res.*, 67(8):3898-903 (2007); Haga-Friedman et al., *J. Immu.*, 188: 5538-5546 (2012)). The full length α and β chains of each of the four TCRs, including these modifications to the constant region, are shown in Table 8. In Table 8, the CDRs are underlined, and the modified amino acid residues of the constant region are underlined and in bold.

TABLE 8

| SEQ ID NO: 29 (Cys-substituted, LVL-modified 4304 TCR1 α chain with N-terminal signal peptide) | MKPTLISVLVIIFILRGTRAQRVTQPEKLLSVFKGAPVELKCNYSYSGSPEL FWYVQYSRQRLQLLLRHISRESIKGFTADLNKGETSFHLKKPFAQEEDSA MYYCALLQGAQKLVFGQGTRLTINPNIQNPEPAVYQLKDPRSQDSTLCLF TDFDSQINVPKTMESGTFITDKCVLDMKAMDSKSNGAIAWSNQTSFTCQ DIFKETNATYPSSDVPCDATLTEKSFETDMNLNFQNLLVIVLRILLLKVAG FNLLMTLRLWSS |
|---|---|
| SEQ ID NO: 30 (Cys-substituted, LVL-modified 4304 TCR1 β chain with N-terminal signal peptide) | MASLLLLLLGLGSVFSAVISQKPSRDICQRGTSLTIQCQVDSQVTMMFWYR QQPGQSLTLIATANQGSEATYESGFVIDKFPISRPNLTFSTLTVSNMSPED SSIYLCSVESGQDYGYTFGSGTRLTVVEDLRNVTPPKVSLFEPSKAEIANK QKATLVCLARGFFPDHVELSWWVNGKEVHSGVCTDPQAYKESNYSYCL SSRLRVSATFWHNPRNHFRCQVQFHGLSEEDKWPEGSPKPVTQNISAEA WGRADCGITSASYQQGVLSATILYEILLGKATLYAVLVSTLVVMAMVKR KNS |
| SEQ ID NO: 31 (Cys-substituted, LVL-modified 4304 TCR1 α chain predicted sequence without N-terminal signal peptide) | AQRVTQPEKLLSVFKGAPVELKCNYSYSGSPELFWYVQYSRQRLQLLLR HISRESIKGFTADLNKGETSFHLKKPFAQEEDSAMYYCALLQGAQKLVFG QGTRLTINPNIQNPEPAVYQLKDPRSQDSTLCLFTDFDSQINVPKTMESGT FITDKCVLDMKAMDSKSNGAIAWSNQTSFTCQDIFKETNATYPSSDVPCD ATLTEKSFETDMNLNFQNLLVIVLRILLLKVAGFNLLMTLRLWSS |
| SEQ ID NO: 32 (Cys-substituted, LVL-modified 4304 TCR1 β chain predicted sequence without N-terminal signal peptide) | SAVISQKPSRDICQRGTSLTIQCQVDSQVTMMFWYRQQPGQSLTLIATAN QGSEATYESGFVIDKFPISRPNLTFSTLTVSNMSPEDSSIYLCSVESGQDY GYTFGSGTRLTVVEDLRNVTPPKVSLFEPSKAEIANKQKATLVCLARGFFP DHVELSWWVNGKEVHSGVCTDPQAYKESNYSYCLSSRLRVSATFWHNP RNHFRCQVQFHGLSEEDKWPEGSPKPVTQNISAEAWGRADCGITSASYQ QGVLSATILYEILLGKATLYAVLVSTLVVMAMVKRKNS |

Nucleotide sequences encoding the variable regions of the α and β chains of the 4304 TCR1 of Table 8 were cloned into an MSGV1-based retroviral vector with the following expression cassette configuration: 5'NcoI-VDJβ-mCβ-Furin/SerGly/P2A-VJα-mCα-EcoRI3'. To facilitate cloning of the TCR expression cassette into the MSGV1 vector 5'NcoI site, the second amino acid in the N-terminal signal peptide of the TCRVβ chain was changed from a leucine (L) to an alanine (A). The nucleotide sequence encoding the TCR α chain comprised SEQ ID NO: 39. The nucleotide sequence encoding the TCR β chain comprised SEQ ID NO: 40.

The TCRβ and TCRα chains were separated by a Furin Ser/Gly P2A linker peptide (SEQ ID NO: 33). Without being bound to a particular theory or mechanism, it is believed that the linker peptide provides comparable expression efficiency of the two chains (Szymczak et al., *Nat. Biotechnol.*, 22(5): 589-94 (2004)).

The TCR expression cassette of the retroviral vector encoded, from 5' to 3', the TCRβ and TCRα chains separated by the linker peptide. The TCR expression cassette comprised the nucleotide sequence of SEQ ID NO: 38. The amino acid sequence encoded by the TCR expression cassette is shown in Table 9. In Table 9, the CDRs are underlined, the constant regions are italicized, and the linker peptide is shown in bold.

TABLE 9

| TCR Name | Amino acid sequence encoded by TCR Expression Cassette |
|---|---|
| 4304 TCR1 | MASLLLLLLGLGSVFSAVISQKPSRDICQRG TSLTIQCQVDSQVTMMFWYRQQPGQSLTLI ATAN<u>QGSEAT</u>YESGFVIDKFPISRPNLTFS TLTVSNMSPEDSSIYLCSVESG<u>QDYGYT</u>FG SGTRLTV*VEDLRNVTPPKVSLFEPSKAEIA NKQKATLVCLARGFFPDHVELSWWVNGKEV HSGVCTDPQAYKESNYSYCLSSRLRVSATF WHNPRNHFRCQVQFHGLSEEDKWPEGSPKP VTQNISAEAWGRADCGITSASYQQGVLSAT ILYEILLGKATLYAVLVSTLVVMAMVKRKN* S<u>RAKRSGSGATNFSLLKQAGDVEENPGP</u>MK PTLISVLVIIFILRGTRAQRVTQPEKLLSV FKGAPVELKCNYSYSGSPELFWYVQYSRQR LQLLLRHISRESIKGFTADLNKGETSPHLK KPFAQE<u>EDSAMYY</u>CALLQGAQKLVFGQGTR LTINP*NIQNPEPAVYQLKDPRSQDSTLCLF TDFDSQINVPKTMESGTFITDKCVLDMKAM DSKSNGAIAWSNQTSFTCQDIFKETNATYP SSDVPCDATLTEKSFETDMNLNFQNLLVIV LRILLLKVAGFNLLMTLRLWSS* (SEQ ID NO: 37) |

Example 3

This example demonstrates the avidity of the TCR expressed by the retroviral vector of Example 2.

Healthy donor PBL were transduced with the retroviral vector of Example 2. Autologous DCs were pulsed for two hours with the G12V 24-mer peptide MTEYKLVVVGAVGVGKSALTIQLI (SEQ ID NO: 34) or the corresponding WT 24-mer peptide MTEYKLVVVGAGGVGKSALTIQLI (SEQ ID NO: 35) at the various concentrations shown in FIGS. 1A-1B. The cells were washed twice and co-cultured overnight with transduced T cells at a ratio of 1:1. IFN-γ secretion was measured by ELISA (FIG. 1A). 4-1BB upregulation was evaluated by fluorescence activated cell sorting (FACS) (FIG. 1B). As shown in FIGS. 1A-1B, the TCR-transduced cells demonstrated specific and avid recognition of the DC pulsed with the G12V 24-mer peptide.

Example 4

This example demonstrates that the TCR expressed by the retroviral vector of Example 2 recognizes G12V RAS presented by an HLA-DRB1*01/HLA-DRA*01 heterodimer.

The MHC Class II molecules expressed by Patient 4304 were determined using exome and mRNA sequencing. The expressed MHC Class II molecules are shown in FIG. 2.

Effector cells were healthy donor PBL transduced with the retroviral vector of Example 2 encoding the 4304 TCR1. Target cells were COST or HEK 293 cells independently transfected with one of the HLA Class II heterodimers shown in FIG. 2. The target cells were loaded with the G12V 24-mer peptide and were cultured in the presence or absence of an antibody which blocked the respective HLA Class II molecule previously transfected. Target cells cultured with DMSO served as a negative control. Autologous DC from patent 4304 treated with (i) the G12V 24-mer peptide in the absence of the HLA blocking antibodies served as a positive control and (ii) DMSO served as a negative control.

Reactivity was tested by IFNγ-secretion using ELISpot assay. The results are shown in FIG. 2. As shown in FIG. 2, reactivity was observed upon co-culture of the 4304 TCR1-transduced cells with the G12V 24-mer-loaded target cells which had been transduced with a nucleotide sequence encoding a DRA*01:01/DRB1*01:01 heterodimer. This reactivity was blocked by an antibody which recognized the DRA*01:01/DRB1*01:01 heterodimer.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. An isolated or purified T-cell receptor (TCR) comprising the amino acid sequences of
    all of SEQ ID NOs: 1-6,
    wherein the TCR has antigenic specificity for a mutated human RAS amino acid sequence with a substitution of glycine at position 12 with valine,
    wherein the mutated human RAS amino acid sequence is a mutated human Kirsten rat sarcoma viral oncogene homolog (KRAS), a mutated human Harvey rat sarcoma viral oncogene homolog (HRAS), or a mutated human Neuroblastoma rat sarcoma viral oncogene homolog (NRAS) amino acid sequence, and
    wherein position 12 is defined by reference to the wild-type human KRAS, wild-type human HRAS, or wild-type human NRAS protein, respectively.

2. The TCR according to claim 1, wherein the mutated human RAS amino acid sequence is MTEYKLVVVGAVGVGKSALTIQLI (SEQ ID NO: 34).

3. The TCR according to claim 1, wherein the TCR does not have antigenic specificity for the wild-type human RAS amino acid sequence of MTEYKLVVVGAGGVGKSALTIQLI (SEQ ID NO: 35).

4. The TCR according to claim 1, wherein the mutated human RAS amino acid sequence is presented by a human leukocyte antigen (HLA) Class II molecule.

5. The TCR according to claim 4, wherein the HLA Class II molecule is an HLA-DR heterodimer.

6. The TCR according to claim 4, wherein the HLA Class II molecule comprises a HLA-DR α chain in combination with a HLA-DR β chain encoded by the HLA-DRB1 gene.

7. The TCR according to claim 4, wherein the HLA Class II molecule is an HLA-DRB1*01: HLA-DRA*01 heterodimer.

8. The TCR according to claim 1, comprising the amino acid sequences of:
    (i) SEQ ID NO: 7,
    (ii) SEQ ID NO: 8,
    (iii) SEQ ID NO: 9,
    (iv) SEQ ID NO: 10,
    (v) both of SEQ ID NOs: 7 and 8, or
    (vi) both of SEQ ID NOs: 9 and 10.

9. The TCR of claim 1, further comprising:
    (a) an α chain constant region comprising the amino acid sequence of SEQ ID NO: 19, wherein:
        (i) X at position 48 of SEQ ID NO: 19 is Thr or Cys;
        (ii) X at position 112 of SEQ ID NO: 19 is Ser, Ala, Val, Leu, Ile, Pro, Phe, Met, or Trp;
        (iii) X at position 114 of SEQ ID NO: 19 is Met, Ala, Val, Leu, Ile, Pro, Phe, or Trp; and
        (iv) X at position 115 of SEQ ID NO: 19 is Gly, Ala, Val, Leu, Ile, Pro, Phe, Met, or Trp;
    (b) a β chain constant region comprising the amino acid sequence of SEQ ID NO: 20, wherein X at position 57 of SEQ ID NO: 20 is Ser or Cys; or
    (c) both (a) and (b).

10. The isolated or purified TCR of claim 1, comprising:
    (a) an α chain comprising the amino acid sequence of SEQ ID NO: 25, wherein:
        (i) X at position 175 of SEQ ID NO: 25 is Thr or Cys;
        (ii) X at position 239 of SEQ ID NO: 25 is Ser, Ala, Val, Leu, Ile, Pro, Phe, Met, or Trp;
        (iii) X at position 241 of SEQ ID NO: 25 is Met, Ala, Val, Leu, Ile, Pro, Phe, or Trp; and
        (iv) X at position 242 of SEQ ID NO: 25 is Gly, Ala, Val, Leu, Ile, Pro, Phe, Met, or Trp;

(b) a β chain comprising the amino acid sequence of SEQ ID NO: 26, wherein X at position 186 of SEQ ID NO: 26 is Ser or Cys;
    (c) both (a) and (b);
    (d) an α chain comprising the amino acid sequence of SEQ ID NO: 27, wherein:
        (i) X at position 156 of SEQ ID NO: 27 is Thr or Cys;
        (ii) X at position 220 of SEQ ID NO: 27 is Ser, Ala, Val, Leu, Ile, Pro, Phe, Met, or Trp;
        (iii) X at position 222 of SEQ ID NO: 27 is Met, Ala, Val, Leu, Ile, Pro, Phe, or Trp; and
        (iv) X at position 223 of SEQ ID NO: 27 is Gly, Ala, Val, Leu, Ile, Pro, Phe, Met, or Trp;
    (e) a β chain comprising the amino acid sequence of SEQ ID NO: 28, wherein X at position 171 of SEQ ID NO: 28 is Ser or Cys;
    (f) both (d) and (e);
    (g) SEQ ID NO: 29;
    (h) SEQ ID NO: 30;
    (i) SEQ ID NO: 31;
    (j) SEQ ID NO: 32;
    (k) both (g) and (h); or
    (l) both (i) and (j).

11. An isolated or purified polypeptide comprising a functional portion of the TCR of claim 1, wherein the functional portion comprises the amino acid sequences of all of SEQ ID NOs: 1-6.

12. The isolated or purified polypeptide according to claim 11, wherein the functional portion comprises the amino acid sequence(s) of:
    (i) SEQ ID NO: 7,
    (ii) SEQ ID NO: 8,
    (iii) SEQ ID NO: 9,
    (iv) SEQ ID NO: 10,
    (v) both of SEQ ID NOs: 7 and 8, or
    (vi) both of SEQ ID NOs: 9 and 10.

13. The isolated or purified polypeptide of claim 11, further comprising:
    (a) the amino acid sequence of SEQ ID NO: 19, wherein:
        (i) X at position 48 of SEQ ID NO: 19 is Thr or Cys;
        (ii) X at position 112 of SEQ ID NO: 19 is Ser, Ala, Val, Leu, Ile, Pro, Phe, Met, or Trp;
        (iii) X at position 114 of SEQ ID NO: 19 is Met, Ala, Val, Leu, Ile, Pro, Phe, or Trp; and
        (iv) X at position 115 of SEQ ID NO: 19 is Gly, Ala, Val, Leu, Ile, Pro, Phe, Met, or Trp;
    (b) the amino acid sequence of SEQ ID NO: 20, wherein X at position 57 of SEQ ID NO: 20 is Ser or Cys; or
    (c) both (a) and (b).

14. The isolated or purified polypeptide of claim 11, comprising:
    (a) an α chain comprising the amino acid sequence of SEQ ID NO: 25, wherein:
        (i) X at position 175 of SEQ ID NO: 25 is Thr or Cys;
        (ii) X at position 239 of SEQ ID NO: 25 is Ser, Ala, Val, Leu, Ile, Pro, Phe, Met, or Trp;
        (iii) X at position 241 of SEQ ID NO: 25 is Met, Ala, Val, Leu, Ile, Pro, Phe, or Trp; and
        (iv) X at position 242 of SEQ ID NO: 25 is Gly, Ala, Val, Leu, Ile, Pro, Phe, Met, or Trp;
    (b) a β chain comprising the amino acid sequence of SEQ ID NO: 26, wherein X at position 186 of SEQ ID NO: 26 is Ser or Cys;
    (c) both (a) and (b);
    (d) an α chain comprising the amino acid sequence of SEQ ID NO: 27, wherein:
        (i) X at position 156 of SEQ ID NO: 27 is Thr or Cys;

(ii) X at position 220 of SEQ ID NO: 27 is Ser, Ala, Val, Leu, Ile, Pro, Phe, Met, or Trp;

(iii) X at position 222 of SEQ ID NO: 27 is Met, Ala, Val, Leu, Ile, Pro, Phe, or Trp; and (iv) X at position 223 of SEQ ID NO: 27 is Gly, Ala, Val, Leu, Ile, Pro, Phe, Met, or Trp;

(e) a β chain comprising the amino acid sequence of SEQ ID NO: 28, wherein X at position 171 of SEQ ID NO: 28 is Ser or Cys;

(f) both (d) and (e);

(g) SEQ ID NO: 29;

(h) SEQ ID NO: 30;

(i) SEQ ID NO: 31;

(j) SEQ ID NO: 32;

(k) both (g) and (h); or (l) both (i) and (j).

15. An isolated or purified protein comprising a first polypeptide chain comprising the amino acid sequences of SEQ ID NOs: 1-3 and a second polypeptide chain comprising the amino acid sequences of SEQ ID NOs: 4-6.

16. The isolated or purified protein according to claim 15, wherein:

(i) the first polypeptide chain comprises the amino acid sequence of SEQ ID NO: 7 and the second polypeptide chain comprises the amino acid sequence of SEQ ID NO: 8; or (ii) the first polypeptide chain comprises the amino acid sequence of SEQ ID NO: 9 and the second polypeptide chain comprises the amino acid sequence of SEQ ID NO: 10.

17. The isolated or purified protein of claim 15, wherein:

(a) the first polypeptide chain further comprises the amino acid sequence of SEQ ID NO: 19, wherein:

(i) X at position 48 of SEQ ID NO: 19 is Thr or Cys;

(ii) X at position 112 of SEQ ID NO: 19 is Ser, Ala, Val, Leu, Ile, Pro, Phe, Met, or Trp;

(iii) X at position 114 of SEQ ID NO: 19 is Met, Ala, Val, Leu, Ile, Pro, Phe, or Trp; and (iv) X at position 115 of SEQ ID NO: 19 is Gly, Ala, Val, Leu, Ile, Pro, Phe, Met, or Trp;

(b) the second polypeptide chain further comprises the amino acid sequence of SEQ ID NO: 20, wherein X at position 57 of SEQ ID NO: 20 is Ser or Cys; or (c) both (a) and (b).

18. The isolated or purified protein of claim 15, wherein:

(a) the first polypeptide chain comprises the amino acid sequence of SEQ ID NO: 25, wherein:

(i) X at position 175 of SEQ ID NO: 25 is Thr or Cys;

(ii) X at position 239 of SEQ ID NO: 25 is Ser, Ala, Val, Leu, Ile, Pro, Phe, Met, or Trp;

(iii) X at position 241 of SEQ ID NO: 25 is Met, Ala, Val, Leu, Ile, Pro, Phe, or Trp; and (iv) X at position 242 of SEQ ID NO: 25 is Gly, Ala, Val, Leu, Ile, Pro, Phe, Met, or Trp;

(b) the second polypeptide chain comprises the amino acid sequence of SEQ ID NO: 26, wherein X at position 186 of SEQ ID NO: 26 is Ser or Cys;

(c) both (a) and (b);

(d) the first polypeptide chain comprises the amino acid sequence of SEQ ID NO: 27, wherein:

(i) X at position 156 of SEQ ID NO: 27 is Thr or Cys;

(ii) X at position 220 of SEQ ID NO: 27 is Ser, Ala, Val, Leu, Ile, Pro, Phe, Met, or Trp;

(iii) X at position 222 of SEQ ID NO: 27 is Met, Ala, Val, Leu, Ile, Pro, Phe, or Trp; and (iv) X at position 223 of SEQ ID NO: 27 is Gly, Ala, Val, Leu, Ile, Pro, Phe, Met, or Trp;

(e) the second polypeptide chain comprises the amino acid sequence of SEQ ID NO: 28, wherein X at position 171 of SEQ ID NO: 28 is Ser or Cys;

(f) both (d) and (e);

(g) the first polypeptide chain comprises the amino acid sequence of SEQ ID NO: 29;

(h) the second polypeptide chain comprises the amino acid sequence of SEQ ID NO: 30;

(i) the first polypeptide chain comprises the amino acid sequence of SEQ ID NO: 31;

(j) the second polypeptide chain comprises the amino acid sequence of SEQ ID NO: 32;

(k) both (g) and (h); or (l) both (i) and (j).

19. An isolated or purified nucleic acid comprising a nucleotide sequence encoding the TCR according to claim 1.

20. An isolated or purified nucleic acid comprising, from 5' to 3', a first nucleotide sequence and a second nucleotide sequence, wherein the first and second nucleotide sequence, respectively, encode the amino sequences of SEQ ID NOs: 7 and 8; 8 and 7; 9 and 10; 10 and 9; 25 and 26; 26 and 25; 27 and 28; 28 and 27; 29 and 30; 30 and 29; 31 and 32; or 32 and 31.

21. The isolated or purified nucleic acid according to claim 20, further comprising a third nucleotide sequence interposed between the first and second nucleotide sequence, wherein the third nucleotide sequence encodes a cleavable linker peptide.

22. The isolated or purified nucleic acid according to claim 21, wherein the cleavable linker peptide comprises the amino acid sequence of RAKRSGSGATNFSLLKQAGD-VEENPGP (SEQ ID NO: 33).

23. A recombinant expression vector comprising the nucleic acid according to claim 19.

24. The recombinant expression vector according to claim 23, which is a transposon or a lentiviral vector.

25. An isolated or purified TCR encoded by the nucleic acid according to claim 19.

26. An isolated or purified TCR, polypeptide, or protein TCR that results from expression of the nucleic acid according to claim 19 in a cell.

27. A method of producing a host cell expressing a TCR that has antigenic specificity for the peptide of MTEYKLVVVGAVGVGKSALTIQLI (SEQ ID NO: 34), the method comprising contacting a cell with the vector according to claim 23 under conditions that allow introduction of the vector into the cell.

28. An isolated or purified host cell comprising the nucleic acid according to claim 19.

29. The host cell according to claim 28, wherein the cell is a human lymphocyte.

30. The host cell according to claim 28, wherein the cell is selected from the group consisting of a T cell, a natural killer T (NKT) cell, an invariant natural killer T (iNKT) cell, and a natural killer (NK) cell.

31. An isolated or purified population of cells comprising the host cell according to claim 28.

32. A method of producing a TCR, the method comprising culturing the host cell according to claim 28, so that the TCR is produced.

33. A pharmaceutical composition comprising (a) the population of cells according to claim 31 and (b) a pharmaceutically acceptable carrier.

34. A method of detecting the presence of cancer in mammal, the method comprising:

(a) contacting a sample comprising cells of the cancer with the TCR according to claim 1, thereby forming a complex; and (b) detecting the complex, wherein detection of the complex is indicative of the presence of cancer in the mammal.

35. A method of inducing an immune response against cancer in a mammal, the method comprising administering to the mammal the population of cells according to claim 31 in an amount effective to induce the immune response against cancer in the mammal.

36. A method of treating cancer in a mammal, the method comprising administering to the mammal the population of cells according to claim 31 in an amount effective to treat cancer in the mammal.

37. The method of claim 36, wherein the cancer expresses a mutated human RAS amino acid sequence with a substitution of glycine at position 12 with valine, wherein the mutated human RAS amino acid sequence is a mutated human Kirsten rat sarcoma viral oncogene homolog (KRAS), a mutated human Harvey rat sarcoma viral oncogene homolog (HRAS), or a mutated human Neuroblastoma rat sarcoma viral oncogene homolog (NRAS) amino acid sequence, and wherein position 12 is defined by reference to the wild-type human KRAS, wild-type human HRAS, or wild-type human NRAS protein, respectively.

38. The method of claim 37, wherein the mutated human RAS amino acid sequence is a mutated human Kirsten rat sarcoma viral oncogene homolog (KRAS) amino acid sequence.

39. The method of claim 37, wherein the mutated human RAS amino acid sequence is a mutated human neuroblastoma rat sarcoma viral oncogene homolog (NRAS) amino acid sequence.

40. The method of claim 37, wherein the mutated human RAS amino acid sequence is a mutated human Harvey rat sarcoma viral oncogene homolog (HRAS) amino acid sequence.

41. The method according to claim 37, wherein the cancer is pancreatic, colorectal, lung, endometrial, ovarian, or prostate cancer.

* * * * *